United States Patent [19]
Kaiser et al.

[11] Patent Number: 6,031,117
[45] Date of Patent: Feb. 29, 2000

[54] BORONIC ACID CONTAINING PHOSPHORAMIDITE REAGENTS

[75] Inventors: Robert J. Kaiser, Bothell; Mark L. Stolowitz, Woodinville, both of Wash.

[73] Assignee: Prolinx Incorporated, Bothell, Wash.

[21] Appl. No.: 09/272,978

[22] Filed: Mar. 19, 1999

[51] Int. Cl.[7] ........................................................ C07F 5/04

[52] U.S. Cl. ............................ 552/105; 558/72; 558/288; 558/290

[58] Field of Search ............................... 552/105; 558/72, 558/288, 290

[56] References Cited

U.S. PATENT DOCUMENTS 3,222,379  12/1965  Farthouat ............................. 558/288 X

*Primary Examiner*—Michael G. Ambrose
*Attorney, Agent, or Firm*—Townsend and Townsend and Crew LLP

[57] ABSTRACT

The present invention provides arylboronic acid reagents useful for incorporation into modified oligonucleotides and polynucleotides. The modified oligonucleotides and polynucleotides thus produced are useful in bioconjugation reactions for the immobilization and purification of macromolecules.

14 Claims, 8 Drawing Sheets

↓ N-Benzyloxycarbonyl-beta-alanine
N-Hydroxysuccinimide Ester,
Dimethylformamide, Diisopropylethylamine ↓ 4,4'-Dimethoxytrityl Chloride, Pyridine ↓ Lithium Borohydride, Tetrahydrofuran ↓ Hydrogen, Palladium on Carbon, Methanol Figure 8. Example of HPLC purified PBA-modified oligodeoxyribonucleotides (PBA1-4 PX001)
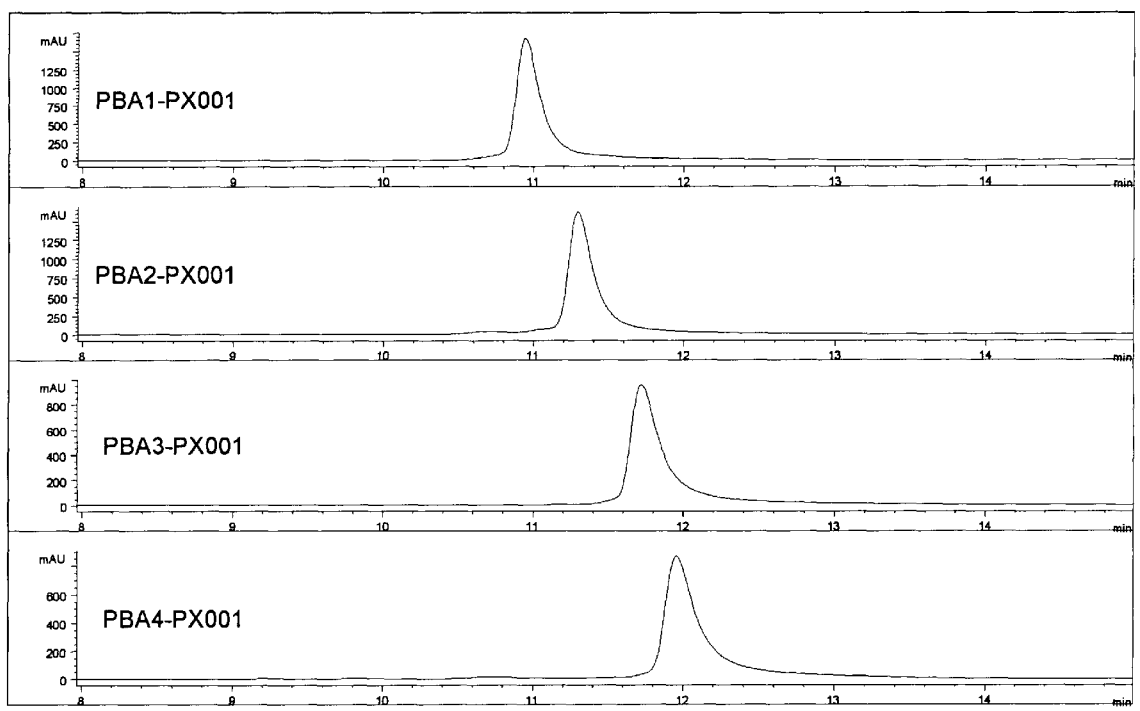

BORONIC ACID CONTAINING PHOSPHORAMIDITE REAGENTS

FIELD OF INVENTION

The present invention relates to the field of nucleic acid immobilization, purification and detection and, more particularly, to reagents for the introduction of boronic acids into modified oligonucleotides and polynucleotides.

BACKGROUND OF THE INVENTION

Arylboronic acids, such as phenylboronic acids, are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to occur with either neutral phenylboronic acid or phenylboronate anion. Immobilized phenylboronic acids have been used as chromatographic supports to selectively retain, from diverse biological samples, those molecular species having the requisite functionalities. Many important biological molecules including, but not limited to, carbohydrates, catecholamines, prostaglandins, ribonucleosides, and steroids contain the requisite functionalities, and have been either analyzed or purified in this manner. The use of phenylboronic acid chromatographic media for the isolation and separation of biological molecules has been discussed in several reviews (see, Singhal, R. P. and DeSilva, S. S. M. (1992) *Adv. Chromatog.*, 31, 293–335; Mazzeo, J. R. and Krull, I. S. (1989) *BioChromatog.*, 4, 124–130; and Bergold, A. and Scouten, W. H. (1983) in *Solid Phase Biochemistry* (Scouten, W. H. ed.) pp. 149–187, John Wiley & Sons, New York).

Molecular species having cis or coaxial 1,2-diol and 1,3-diol functionalities, and particularly carbohydrates, are known to complex with immobilized compounds having a phenylboronate anion to form cyclic esters under alkaline aqueous conditions (see, Lorand, J. P. and Edwards, J. O. (1959) *J. Org. Chem.*, 24, 769). In addition, carbohydrate binding to arylboronic acid moieties is known to induce fluorescence changes by enhancing the electronic interaction between an arylboronic acid and an amine functionality contained within the arylboronic acid (see, T. D. James et al. (1994) *J. Chem. Soc. Chem. Comm.*, 477–478).

In view of their ability to complex to biomolecules, such as biological macromolecules, reagents derived from arylboronic acids are useful in a variety of bioconjugation applications involving immobilization, purification and detection. Bioconjugation is a descriptive term for the joining of two or more different molecular species by chemical or biological means, in which at least one of the molecular species is a biological macromolecule. Bioconjugation includes, but is not limited to, the conjugation of proteins, peptides, polysaccharides, hormones, nucleic acids, liposomes and cells with each other or with any other molecular species that add useful properties. Immobilization of biological macromolecules is also considered a special case of bioconjugation, in which the macromolecule is conjugated, either reversibly or irreversibly, to an insoluble support. Bioconjugation is utilized extensively in biochemical, immunochemical and molecular biological research. Major applications of bioconjugation include, but are not limited to, detection of gene probes, enzyme-linked immuno solid-phase assay (ELISA), monoclonal antibody drug targeting and medical imaging.

In most instances, bioconjugation is based upon known reactions between two binding partners making a binding pair. One example of a bioconjugation reaction involves a first binding partner, e.g., an ortho-substituted acetamidophenylboronic acid, and a second binding partner, e.g., the vicinal diol moieties of the carbohydrate residues associated with glycoproteins (see, Cai, S. X. and Keana, J. F. W. (1991) *Bioconjugate Chem.*, 2, 317–322).

In addition, phenylboronic acid bioconjugates derived from 3-isothiocyanatophenylboronic acid have been successfully utilized for appending radioactive technetium dioxime complexes to monoclonal antibodies for use in medical imaging (see, Linder, K. E., Wen, M. D., Nowotnik, D. P., Malley, M. F., Gougoutas, J. Z., Nunn, A. D. and Eckelman, W. C. (1991) *Bioconjugate Chem.*, 2, 160–170; Linder, K. E., Wen, M. D., Nowotnik, D. P., Ramalingam, K., Sharkey, R. M., Yost, F., Narra, R. K. and Eckelman, W. C. (1991) *Bioconjugate Chem.*, 2, 407–414).

Moreover, boronic acid reagents have exhibited broad utility as bioconjugation reagents when utilized in conjunction with newly developed boronic acid complexing reagents derived from salicylhydroxamic acid (SHA) and 2,6-dihydroxybenzohydroxamic acid (DHBHA). Boronic acid reagents, boronic acid complexing reagents, their conjugates and bioconjugates, as well as methods for their preparation and use are disclosed in U.S. Pat. Nos. 5,594,111, 5,623,055, 5,668,258, 5,648,470, 5,594,151, 5,668,257, 5,677,431, 5,688,928, 5,744,627, 5,777,148, 5,831,045 and 5,831,046.

In view of the usefulness of arylboronic acids in bioconjugation reactions, what is needed in the art are boronic acid compounds amenable to incorporation into synthetic oligonucleotides, such as during automated solid phase synthesis. The boronic acid-modified oligonucleotides thus produced would be useful in bioconjugation reactions, such as the immobilization, purification and detection of macromolecules. The present invention fulfills these and other needs.

SUMMARY OF THE INVENTION

Reagents derived from arylboronic acids are useful in a variety of bioconjugation applications as a result of their ability to complex to biological macromolecules. The present invention extends the breath of boronic acid reagents available and includes reagents useful for the preparation of boronic acid-modified synthetic oligonucleotides. As such, in one aspect, the present invention relates compounds having the general structure of Formula I

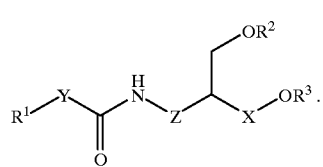

In Formula I, $R^1$ is a functional group including, but not limited to, an arylboronic acid ester moiety, such as a phenylboronic acid ester. Y, in Formula I, is a functional group including, but not limited to, $O(CH_2)_m$, $S(CH_2)_m$, and a carbon-carbon single bond, wherein m is an integer having a value ranging from about 1 to about 5. As used herein, when Y is a carbon-carbon single bond, $R^1$ is directly bonded to the carbonyl group. Z, in Formula I, is a functional group including, but not limited to, alkylene, alkyleneamido, alkyleneamidoalkylene and alkyleneamidoalkyleneamido having between 1 and 16 carbons atoms. X, in Formula I, is a functional group including, but not limited to, a methylene group and a carbon-carbon single bond. When X is a carbon-carbon single bond, the methine carbon in Formula I is directly bonded to $OR^3$. $R^2$, in Formula I, is a functional group including, but not limited to, hydrogen, trityl, monomethoxytrityl and dimethoxytrityl. $R^3$, in Formula I, is a functional group including, but not limited to, a hydrogen or an activated phosphorous moiety.

The arylboronic acid compounds of Formula I are useful in the synthesis of oligonucleotides during automated solid phase synthesis. The oligonucleotides thus produced are useful in a variety of bioconjugation reactions, such as for the immobilization, purification and detection of nucleic acids. The oligonucleotides can be synthesized with the compounds of Formula I appended to the 3' end or the 5' end of the oligonucleotide or polynucleotide.

As such, in another aspect, the present invention provides oligonucleotides having a modified 5' end and having the following general formula In Formula II, R is a functional group including, but not limited to, an arylboronic acid moiety, such as a phenylboronic acid. Y, in Formula II, is a functional group including, but not limited to, $O(CH_2)_m$, $S(CH_2)_m$, and a carbon-carbon single bond, wherein m is an integer having a value ranging from about 1 to about 5. Z, in Formula II, is a functional group including, but not limited to, alkylene, alkyleneamido, alkyleneamidoalkylene and alkyleneamidoalkyleneamido having between 1 and 16 carbons atoms. X, in Formula II, is a functional group including, but not limited to, a methylene group and a carbon—carbon single bond. $R^6$, in Formula II, is a functional group including, but not limited to, hydrogen and hydroxyl. $R^7$, in Formula II, is a functional group including, but not limited to, hydroxyl and a monophosphate ester. The index n, in Formula II, is an integer ranging from about 0 to about 10. The index, n', in Formula II, is an integer ranging from about 10 to about 10000. Nu' and Nu", in Formula II, are independently selected nucleoside bases including, but not limited to, adenine, guanine, thymine, cytosine, uracil and nucleotide analogs. The variables R, Y and X can be the same or different for any given monomeric value of n. The variables $R^6$ and Nu' can be the same or different for any given monomeric value of n'.

In still yet another aspect, the present invention provides oligonucleotides having a modified 3' end and having the following general formula

II

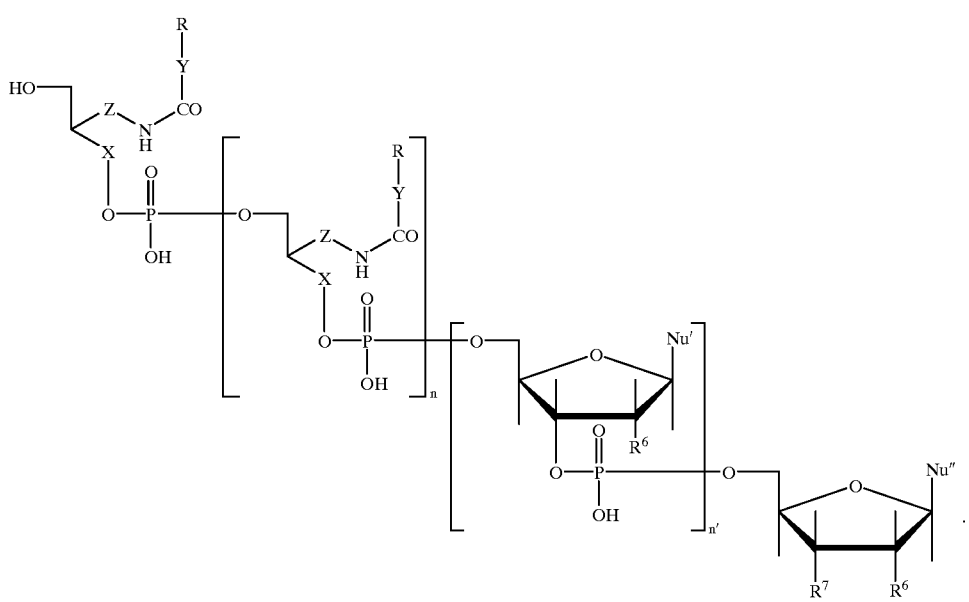

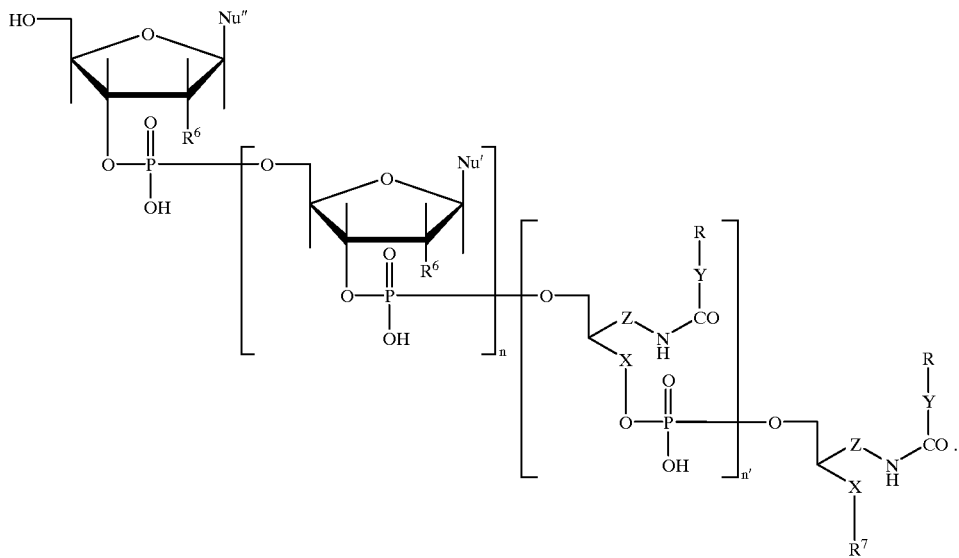

III

In Formula III, R is a functional group including, but not limited to, an arylboronic acid moiety, such as a phenylboronic acid. Y, in Formula III, is a functional group including, but not limited to, $O(CH_2)_m$, $S(CH_2)_m$, and a carbon-carbon single bond, wherein m is an integer having a value ranging from about 1 to about 5. Z, in Formula II, is a functional group including, but not limited to, alkylene, alkyleneamido, alkyleneamidoalkylene and alkyleneamidoalkyleneamido having between 1 and 16 carbons atoms. X, in Formula III, is a functional group including, but not limited to, a methylene group and a carbon-carbon single bond. $R^6$, in Formula III, is a functional group including, but not limited to, hydrogen and hydroxyl. $R^7$, in Formula III, is a functional group including, but not limited to, hydroxyl and a monophosphate ester. The index n, in Formula III, is an integer having a value ranging from about 0 to about 10. The index, n', in Formula II, is an integer having a value ranging from about 10 to about 10000. Nu' and Nu", in Formula III, are independently selected nucleoside bases including, but not limited to, adenine, guanine, thymine, cytosine, uracil and nucleotide analogs. The variables R, Y and X can be the same or different for any given monomeric value of n. The variables $R^6$ and Nu' can be the same or different for any given monomeric value of n'.

These and other aspects of the present invention will become more readily apparent when read with the accompanied detailed description that follows.

BRIEF DESCRIPTION OF THE DRAWINGS

FIG. 8 illustrates the high performance liquid chromatographic purification of four boronic acid-modified oligonucleotides prepared by automated synthesis having 1, 2, 3 and 4 arylboronic acid moieties at the 5'-terminus.

DETAILED DESCRIPTION OF THE INVENTION AND PREFERRED EMBODIMENTS

I. GLOSSARY

Figure 1:
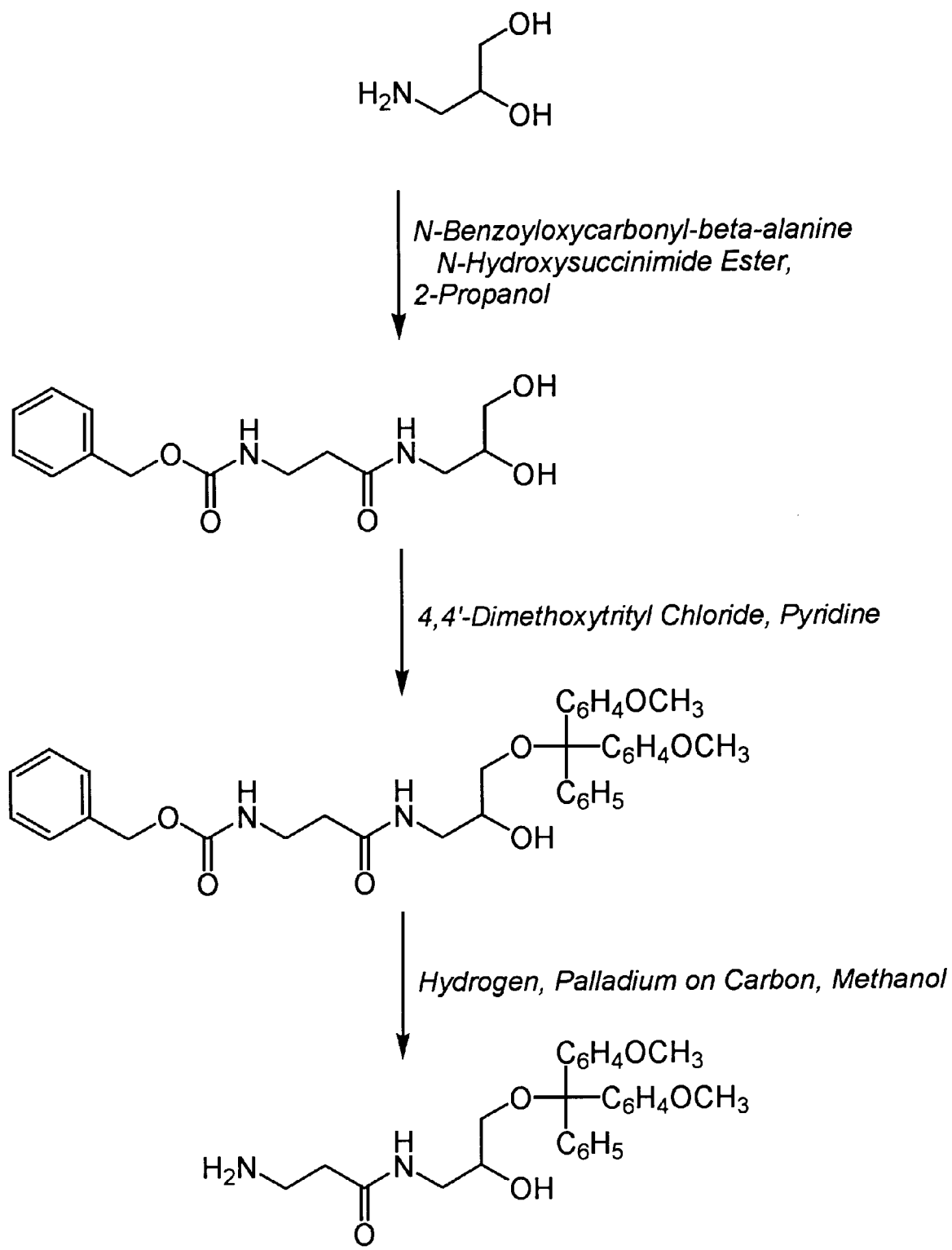
FIG. 1 summarizes a synthetic method to prepare 1-O-(4,4'-dimethoxytrityl)-3-(β-alanyl)amino-1,2-propanediol, a compound of the present invention.
Figure 2:
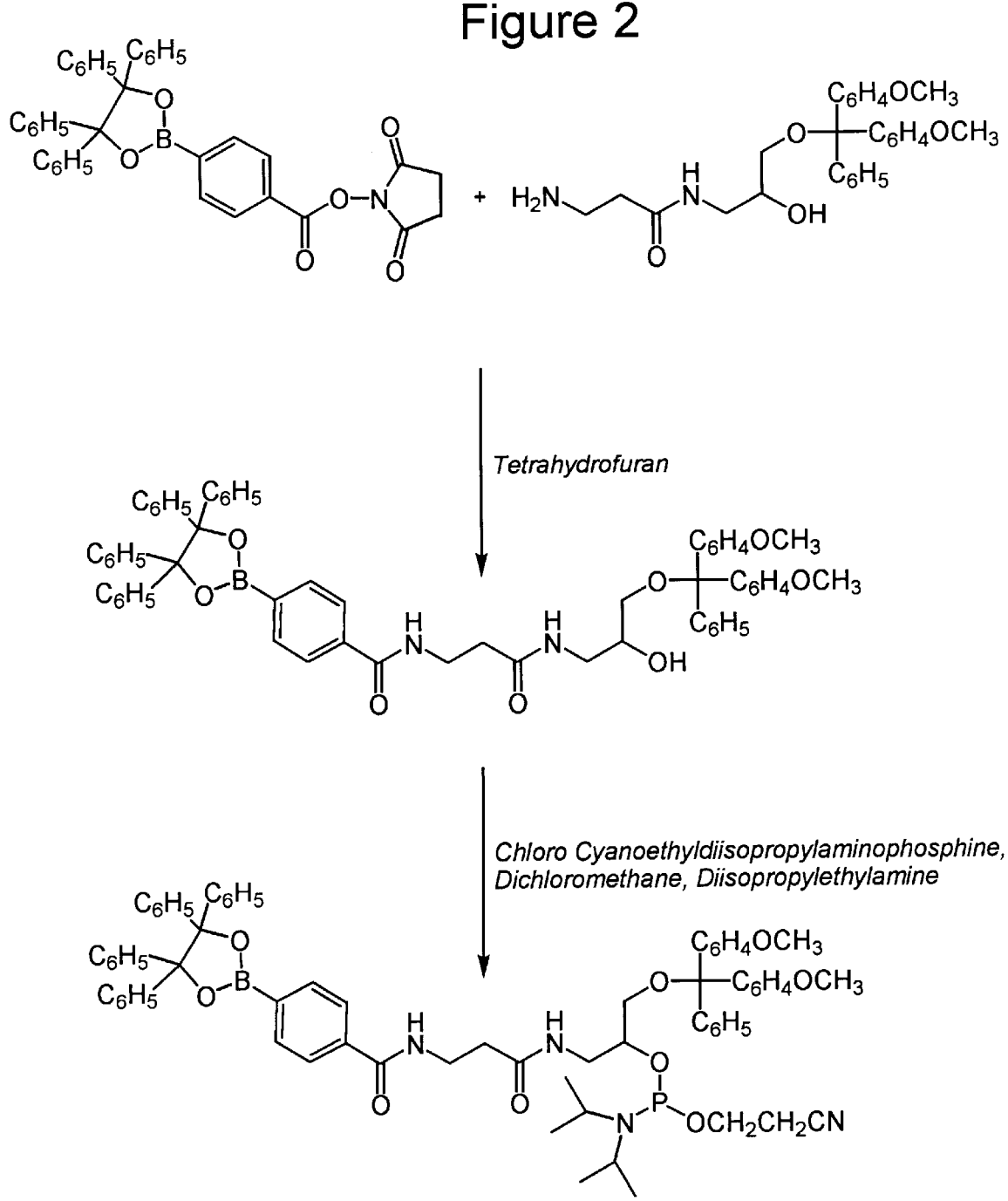
FIG. 2 summarizes a synthetic method to prepare 1-O-(4,4'-dimethoxytrityl)-3-N-[(4-dihydroxy-boryl (benzopinacol cyclic ester)benzoyl)-β-alanyl]amino-1,2-propanediol 3-O-(2-cyanoethyl)-N,N-diisopropylamino phosphoramidite, a compound of the present invention.
Figure 3:
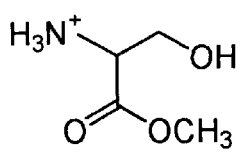
FIG. 3 summarizes a synthetic method to prepare 1-O-(4,4'-dimethoxytrityl)-β-alanylserinol, a compound of the present invention.
Figure 3:
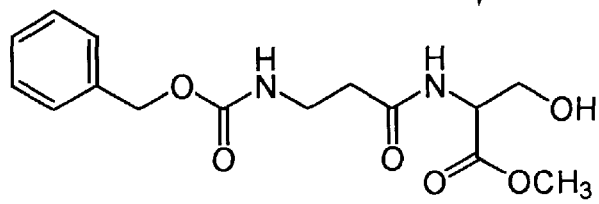
Figure 3:
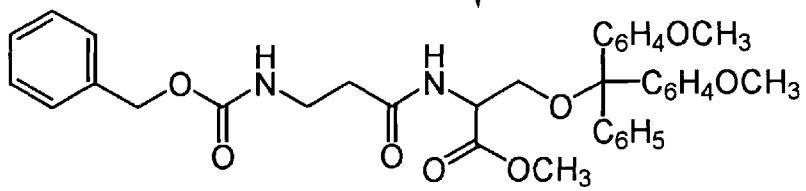
Figure 3:
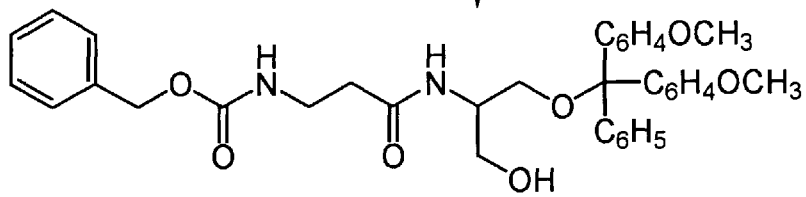
Figure 3:
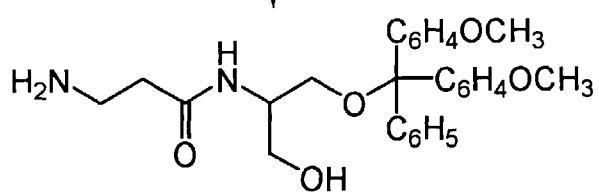

As used herein, the term "alkyl" denotes branched or unbranched hydrocarbon chains, such as methyl, ethyl, n-propyl, iso-propyl, n-butyl, sec-butyl, iso-butyl, tert-butyl, octa-decyl and 2-methylpentyl. These groups can be optionally substituted with one or more functional groups that are commonly attached to such alkyl groups, such as hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene ($—CH_2—$), propylene ($—CH_2CH_2CH_2—$), chloroethylene ($—CHClCH_2—$), 2-thiobutene —CH$_2$CH(SH)CH$_2$CH$_3$, 1-bromo-3-hydroxyl-4-methylpentene (—CHBrCH$_2$CH(OH)CH(CH$_3$)CH$_2$—), having between 1 and 20 carbon atoms and preferrably from about 1 to 16 carbon atoms.

The term "alkyleneamido" refers to a —(CH$_2$)$_n$NC(O) or —(CH$_2$)$_n$C(O)N group, wherein n is about 1 to about 20 and preferrably, from about 1 to 16.

The term "alkyleneamidoalkylene" refers to a —(CH$_2$)$_n$NC(O)(CH$_2$)$_n$ or —(CH$_2$)$_n$C(O)N(CH$_2$)$_n$ group, wherein n is about 1 to about 20 and preferrably, from about 1 to 16.

The term "alkyleneamidoalkyleneamido" refers to a (CH$_2$)$_n$NC(O)(CH$_2$)$_n$NC(O) or —(CH$_2$)$_n$C(O)N(CH$_2$)$_n$C(O)N or (CH$_2$)$_n$NC(O)(CH$_2$)$_n$C(O)N or —(CH$_2$)$_n$C(O)N(CH$_2$)$_n$NC(O), wherein n is about 1 to about 20 and preferrably, from about 1 to 16.

The term "aryl" denotes a chain of carbon atoms which form at least one aromatic ring having preferably between about 6–14 carbon atoms, such as phenyl, naphthyl, and the like, and which may be substituted with one or more functional groups that are commonly attached to such aryl groups, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR, wherein R is alkyl.

The term "amido" denotes the amide linkage: —C(O)NR—, wherein R is hydrogen or alkyl.

The term "amino" denotes an amine linkage: —NR—, wherein R is hydrogen or alkyl.

The term "nucleotide monomer," as used herein refers to the "standard" nucleotides, i.e., adenosine, guanosine, cytidine, thymidine, and uracil, and derivatives of these nucleotides. Such derivatives include, but are not limited to, inosine, 5-bromodeoxycytidine, 5-bromo-deoxyuridine, N6-methyl-deoxyadenosine, 5-methyl-deoxycytidine and the like.

As used herein, the term "protecting group" refers to a group that is joined to or substituted for a reactive group (e.g., a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example Greene et al., *Protective Groups in Organic Synthesis,* 2nd ed., John Wiley & Sons, Inc. Somerset, N.J. (1991).

II. COMPOUNDS

In certain aspects, this invention provides novel arylboronic acid derivatives that, are useful as reagents in the synthesis of polynucleotides and oligonucleotides that in turn, are useful in bioconjugation reactions. The incorporation of these arylboronic acid reagents into oligonucleotides will enable the oligonucleotides to participate in bioconjugation reactions that include, but are not limited to, the conjugation of biomolecules such as proteins, peptides, polysaccharides, hormones, nucleic acids, liposomes and cells.

As such, in one embodiment, the present invention relates to compounds having the general structure of Formula I:

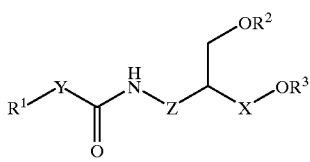

I wherein: $R^1$, Y, Z, X $R^2$ and $R^3$ have been defined previously.

The compounds of Formula I are useful, for example, in automated solid phase oligonucleotide synthesis at high repetitive efficiency. In certain preferred embodiments, highly reactive activated phosphorus moieties and easily removed protecting groups are employed. In certain preferred embodiments, $R^1$ is a phenylboronic acid ester. Certain preferred phenylboronic acid ester moieties include, but not limited to, the following moieties:

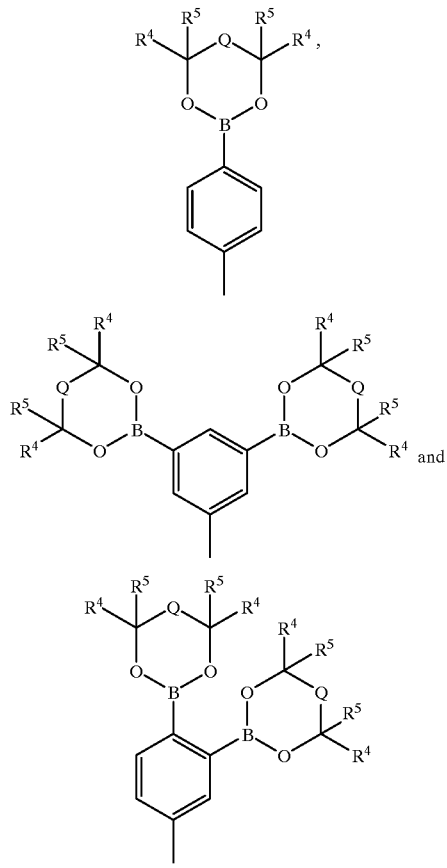

wherein: $R^4$ and $R^5$ are functional groups including, but not limited to, hydrogen, methyl and phenyl. Q is a functional group including, but not limited to, a methylene group and a carbon-carbon single bond. As used herein, when Q is a carbon-carbon single bond, the carbon atoms on either side of Q are bonded directly together.

R³ is a functional group including, but not limited to, hydrogen, and an activated phosphorous moiety including, but not limited to, phosphoramidite, a H-phosphonate, a methyl phosphonate, a phosphorothioate, a phosphotriester, a hemisuccinate, a hemisuccinate covalently bound to a solid support, a cyclohexylcarbodiimide and a cyclohexylcarbodiimide covalently bound to a solid support. Preferably, R³ is a phosphoramidite.

Z is a spacer group having between about 1 to about 16 carbons optionally interrupted by amido groups. In addition, Z can begin and end with an amido group. Preferably, Z is a $C_1$–$C_5$ alkylene group or a $C_1$–$C_5$ alkyleneamido group.

In certain preferred embodiments, X is a methylene group and R² is a dimethoxytrityl group, such as O-(4,4'-dimethoxytrityl). R³ is preferably a phosphoramidite group, such as O-(2-cyanoethyl)-N,N-diisopropylamino phosphoramidite group. A preferred compound of Formula I is 1-O-(4,4'-dimethoxytrityl)-2-N-[(4-dihydroxyboryl(benzopinacol cyclic ester)benzoyl)-β-alanyl)]serinol 3-O-(2-cyanoethyl)-N,N-diisopropylamino phosphoramidite.

The compounds of the present invention are useful in both deoxyribonucleotide and ribonucleotide synthesis to introduce arylboronic acid moieties, such as phenylboronic acid or phenyldiboronic acid moieties, at any position within a synthetic oligonucleotide. In preferred embodiments, the 5' end or the 3' end of an oligonucleotide or polynucleotide is modified. In a preferred embodiment, compounds of Formula I are used to introduce phenylboronic acid or phenyldiboronic acid moieties at the 5' terminus of a synthetic oligonucleotide.

As such, in another embodiment, the present invention relates to compounds having the general structure of Formula II:

wherein: R, Y, Z, X, R⁶, R⁷, n, n', Nu' and Nu" have been previously defined. Moreover, the variables R, Y and X can be the same or different for any given monomeric value of n. In addition, the variables R⁶ and Nu' can be the same or different for any given monomeric value of n'.

In certain preferred embodiments, R, in Formula II, is a phenylboronic acid moiety. Suitable phenylboronic acid moieties include, but are not limited to, the following:

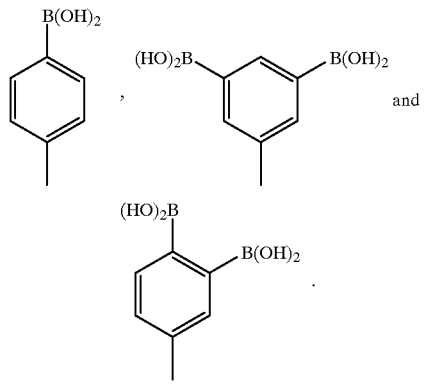

In certain other aspects, the compounds of Formula I are used to introduce arylboronic acids, such as phenylboronic acid or phenyldiboronic acid moieties, at the 3' terminus of a synthetic oligonucleotide or polynucleotide. As such, in another embodiment, the present invention relates to compounds having the general structure of Formula III:

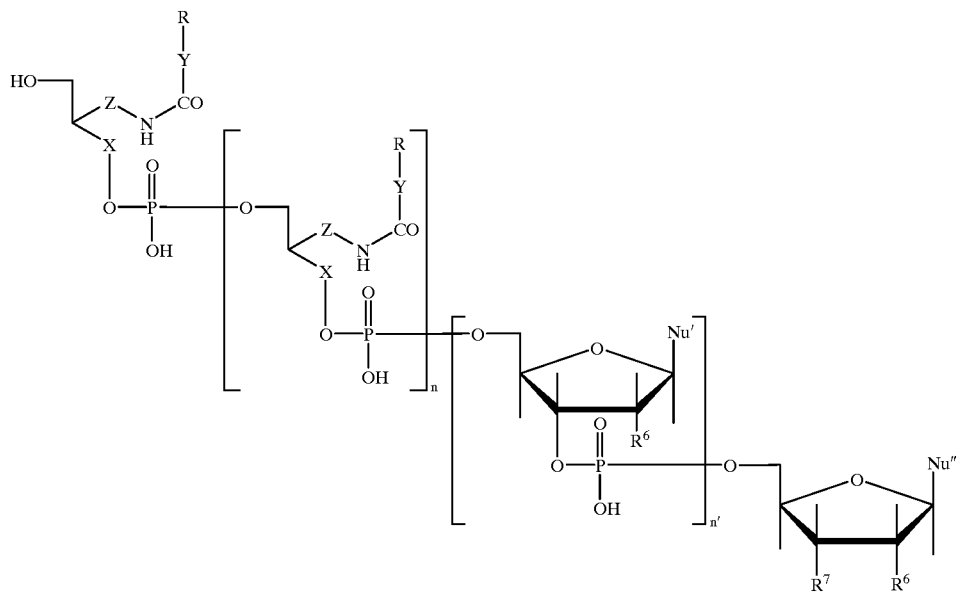

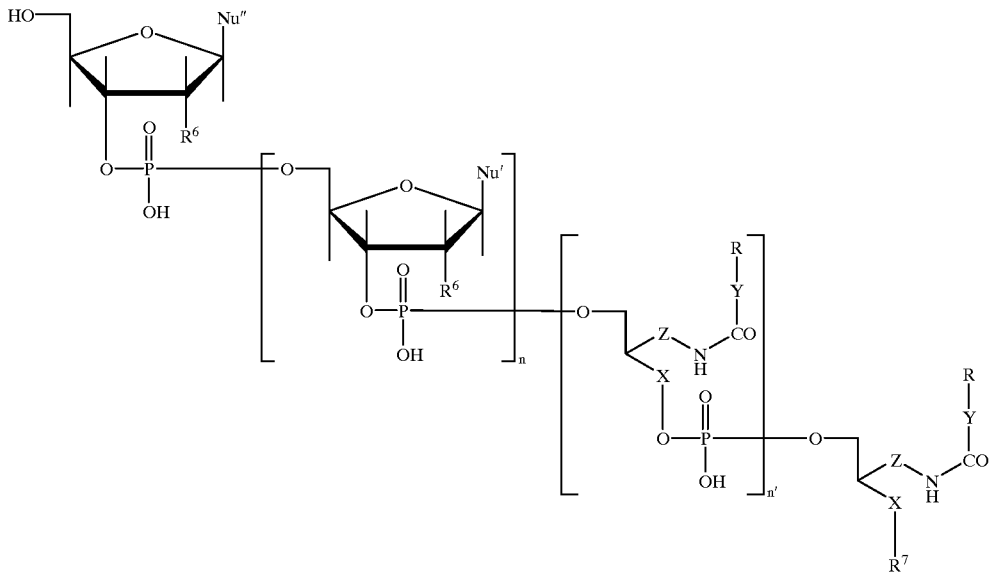

III wherein R, Y, Z, X, $R^6$, $R^7$, n, n', Nu' and Nu" have been previously defined. Moreover, the variables R, Y and X can be the same or different for any given monomeric value of n. In addition, the variables $R^6$ and Nu' can be the same or different for any given monomeric value of n'. R, in Formula III, is preferably a phenylboronic acid moiety. Preferred phenylboronic acid moieties are set forth above with respect to Formula II.

III. SYNTHESIS

Details regarding the syntheses of various compounds of Formula I are set forth in FIGS. 1–7 and, in addition, are described in detail in Examples 1–3 below. The general synthetic strategy is as follows. With reference to FIGS. 1–2 or 3–5, a protected 1,2- or 1,3-diol containing an aliphatic amino group, respectively, is reacted with an activated form (e.g., N-hydroxysuccinimide ester or imidazolide) of a carboxylic acid derivative of a protected arylboronic acid (e.g., phenylboronic acid). The 1,2- or 1,3-amine-containing diol is protected at the 1-hydroxyl with an acid-labile moiety (e.g., 4,4'-dimethoxytrityl). The phenylboronic acid is protected using another 1,2- or 1,3-diol (e.g., 1,3-propanediol, pinacol or benzopinacol) to form a cyclic diester. The resulting product is then reacted with an activated phosphine (e.g., 2-cyanoethyl N,N-diisopropylaminochlorophosphine) to produce the final reactive material useful in oligonucleotide synthesis.

Arylboronic acids, such as phenylboronic acids, that are useful as synthetic intermediates for the preparation of compounds of Formula I are usually prepared in situ by generation of arylmagnesium or aryllithium species from aryl halides followed by transmetalation with a trialkoxyborate (see, Todd, M. H., et al., (1997) *Tetrahedron Lett.*, 38, 6781–6784; Crisofoli, W. A. et al., (1991) *Tetrahedron Lett.*, 32, 5881–5884; Sharp, M. J., et al., (1987) *Tetrahedron Lett.*, 28, 5093–5096; and Larson, R. D., et al., (1994) *J. Org. Chem.*, 59, 6391–6394).

In addition, transition-metal catalyzed cross coupling reactions have been developed to produce phenylboronic acids from aryl halides and alkoxydiboron (see, Ishiyama, T., et al., (1995) *Org. Chem.*, 60, 7508–7510; Giroux, A., et al., (1997) *Tetrahedran Lett.*, 38, 3841–3844) or dialkoxyhydroborane (see, Murata, M.; et al., *J. Org. Chem.* 1997, 62, 6458–6459) using $PdCl_2$ (dppf) as the catalyst. Phenyldiboronic acids which are useful as synthetic intermediates for the preparation of compounds of Formula I are the subject of copending application Ser. No. 09/138,105, filed Aug. 21, 1998.

Once produced, the compounds of Formula I can be used to generate the compounds of Formulae II and III, which can be prepared using methods of automated solid phase synthesis well known to those of skill in the art. For instance, the chemistry of automated solid phase oligonucleotide synthesis, including oligonucleotides containing one or more non-natural modifications such as those provided by compounds of Formula I, is described in the following review articles and reference book: Crockett, G. C. (1983) "The Chemical Synthesis of DNA", *Aldrichimica Acta* 16(3), 47–55; Engels, J. W. and Uhlmann, E. (1989) "Gene Synthesis", *Angew Chem. Int. Ed Engl.* 28, 716–734; Goodchild, J. (1990) "Conjugates of Oligonucleotides and Modified Oligonucleotides: A Review of Their Synthesis and Properties", *Bioconjugate Chem.* 1(3), 165–187; *Oligonucleotide Synthesis: A Practical Approach* (1984) M. J. Gait, ed. (IRL Press Limited: Oxford, England), 217 pp.

In solid state synthesis, the timing of delivery of the compounds of Formula I and their concentrations will not differ from the protocols typical for unmodified commercial phosphoramidites used in commercial DNA synthesizers. One can merely add the solution containing the compounds of Formula I to a receptacle on a port provided for an extra phosphoramidite on a commercial synthesizer (e.g., model 394, Applied Biosystems, Foster City, Calif., USA). However, where the coupling efficiency of a particular compound of Formula I is substantially lower than the other phosphoramidites, it may be necessary to alter the timing of delivery or the concentration of the compounds of Formula I in order to optimize the synthesis. Means of optimizing oligonucleotide synthesis protocols to correct for low coupling efficiencies are well known to those of skill in the art. Generally, one merely increases the concentration of the reagent or the amount of the reagent delivered to achieve a higher coupling efficiency. Methods of determining coupling efficiency are also well known. For example, where the $R^2$ is a dimethoxytrityl (DMT), coupling efficiency can be determined by measuring the DMT cation concentration in the acid step (which removes the DMT group). DMT cation concentration is usually determined by spectrophotometrically monitoring the acid wash. The acid/DMT solution is a bright orange color. Alternatively, since capping prevents further extension of an oligonucleotide where coupling has failed, coupling efficiency can be estimated by comparing the ratio of truncated to full length oligonucleotide utilizing, for example, capillary electrophoresis or HPLC.

Solid phase oligonucleotide synthesis can be performed using a number of solid supports. A suitable support is one that provides a functional group for the attachment of a protected monomer that will become the 3' terminal base in the synthesized oligonucleotide. The support should be inert to the reagents utilized in the particular synthesis chemistry. Suitable supports are well known to those of skill in the art. Solid support materials include, but are not limited to, polacryloylmorpholide, silica, controlled pore glass (CPG), polystyrene, polystyrene/latex, and carboxyl-modified teflon. Preferred supports are amino-functionalized controlled pore glass and carboxyl-functionalized teflon.

Solid phase oligonucleotide synthesis requires, as a starting point, a fully protected monomer (e.g., a protected nucleoside) coupled to the solid support. This coupling is typically through the 3'-hydroxyl (oxo when coupled) covalently bound to a linker which is, in turn, covalently bound to the solid support. The first synthesis cycle then couples a nucleotide monomer, via its 3'-phosphate, to the 5'-hydroxyl of the bound nucleoside through a condensation reaction that forms a 3'-5' phosphodiester linkage. Subsequent synthesis cycles add nucleotide monomers to the 5'-hydroxyl of the last bound nucleotide. In this manner, an oligonucleotide is synthesized in a 3' to 5' direction producing a "growing" oligonucleotide with its 3' terminus attached to the solid support.

Those of skill in the art know numerous means of linking nucleoside monomers to a solid support, although monomers covalently linked through a succinate or hemisuccinate to controlled pore glass are generally preferred. Conventional protected nucleosides coupled through a hemisuccinate to controlled pore glass are commercially available from a number of different sources (e.g., Glen Research, Sterling, Vt., USA; Applied Biosystems, Foster City, Calif., USA; Pharmacia LKB, Piscataway, N.J., USA).

Placement of a compound of Formula I at the 3' end of an oligonucleotide requires initiating oligonucleotide synthesis with a fully blocked compound of Formula I linked to the solid support. Controlled pore glass functionalized with a number of different reactive groups is commercially available (e.g., Sigma Chemical, St. Louis, Mo., USA). A coupling scheme is described by Atkinson et al., chapter 3 in Gait, ed., *Oligonucleotide Synthesis: A Practical Approach*, IRL Press, Washington, D.C. (1984). Triisopropylbenzenesulfonyl chloride, imidazolides, triazolides or even the tetrazolides can also be used as condensing agents. Dicyclohexylcarbodiimide (DCC) and structural analogs are also suitable linkers. Other linkers and appropriate condensing groups are well known to those of skill in the art.

Once the full length oligonucleotide is synthesized, the protecting groups are removed (the oligonucleotide is deprotected), and the oligonucleotide is then cleaved from the solid support prior to use. Cleavage and deprotection can occur simultaneously, or sequentially in any order. The two procedures can be interspersed so that some protecting groups are removed from the oligonucleotide before it is cleaved off the solid support and other groups are deprotected from the cleaved oligonucleotide in solution. The sequence of events depends on the particular blocking groups present, the particular linkage to the solid support, and the preferences of the individuals performing the synthesis. Where deprotection precedes cleavage, the protecting groups can be washed away from the oligonucleotide which remains bound on the solid support. Conversely, where deprotection follows cleavage, the removed protecting groups will remain in solution with the oligonucleotide. Often the oligonucleotide will require isolation from these protecting groups prior to use.

The oligonucleotides of the present invention are not limited to short single stranded sequences. One of skill will recognize that while oligonucleotide synthesis typically has an upper limit of approximately 1,000 bases, preferably about 100 bases, a number of oligonucleotides can be ligated together to form longer sequences. In addition, oligonucleotide having complementary sequences can be hybridized together to form double-stranded molecules. Methods of hybridizing and ligating oligonucleotide to form longer double stranded molecules are well known to those of skill in the art (see, for example, Sambrook et al., *Molecular Cloning—A Laboratory Manual*, Cold Spring Harbor Laboratory, Cold Spring Harbor, N.Y., 1985).

IV. BIOCONJUGATES

As discussed above, the arylboronic acids of Formula I are amenable to incorporation into synthetic oligonucleotides using automated solid phase synthesis to generate compounds of Formulae II and III. The modified oligonucleotides thus produced are useful in bioconjugation reactions including, but are not limited to, the immobilization, purification and detection of macromolecules, such as nucleic acids.

Bioconjugation occurs when two or more molecular species are joined by chemical or biological means. In most instances, bioconjugation is based upon known reactions between two binding partners making a binding pair. For instance, a bioconjugation reaction occurs between an antigen and a binding protein, such as an antibody. Bioconjugation reactions include, but are not limited to, conjugation of proteins, peptides, polysaccharides, hormones, nucleic acids, liposomes and cells, or other biomolecules with each other or with any other molecular species that add useful properties. The modified oligonucleotides and polynucleotides of the present invention are particularly useful as a first binding partner to generate a bioconjugation with respect to immobilization, purification and detection of nucleic acids as second binding partners.

To illustrate bioconjugation using short-hand notation, the first binding partner is a compound of Formulae II or III, which is represented by the following diagram:

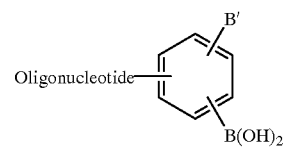

In this diagram, the term "Oligonucleotide" represents an oligonucleotide of Formulae II or III that is about 10 to about 10,000 bases in length, and having from about 1 to about 10 arylboronic acid moieties at either the 3' or 5' terminus, and wherein group B' is either H or a B(OH)$_2$ group.

In this illustrative example, the second binding partner is a molecule derived from 2-hydroxybenzohydroxamic acid (salicylhydroxamic acid), that has appended thereto a conjugate. Suitable conjugates include, but are not limited to, proteins, peptides, polysaccharides, hormones, nucleic acids, liposomes, cells and fluorescent tags. The second binding partner can be depicted as follows:

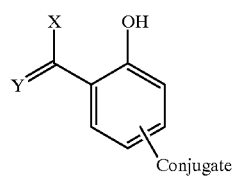

IV

In Formula IV, X is a functional group including, but not limited to, OH, NH$_2$, NHR', NHOH, and NHOR', wherein R' is a functional group including, but not limited to, CH$_3$, CH$_2$CH$_3$, CH$_2$CN, CH$_2$COOH, CH$_2$CONH$_2$ and CH$_2$OCH$_3$. Y is a functional group including, but not limited to, O, S, and NH, and is preferably O.

Compounds of Formula IV and methods for their preparation are disclosed in U.S. Pat. Nos. 5,594,111, 5,594,151, 5,623,055, 5,648,470, 5,668,257, 5,668,258, 5,677,431, 5,688,928 and 5,744,627, as well as copending applications: U.S. patent application Ser. No. 08/488,193, filed Jun. 7, 1995; U.S. patent application Ser. No. 08/577,068, filed Jun. 22, 1995; U.S. patent application Ser. No. 08/689,341, filed Aug. 7, 1996; U.S. patent application Ser. No. 08/956,195, filed Oct. 22, 1997; and U.S. patent application Ser. No. 08/956,204, filed Oct. 22, 1997.

In certain embodiments of the present invention, bioconjugation between an oligonucleotide or polynucleotide of Formula II or Formula III, as a first binding partner, and a conjugate of Formula IV as a second binding partner, will generate a bioconjugate of Formula V as follows:

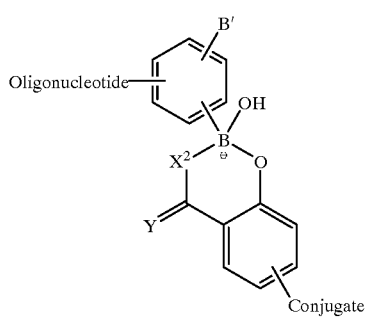

V wherein X$^2$ is O, NH, NR', NOH and NOR' and wherein R' is as defined previously.

Bioconjugates using compounds of Formulae II or III as a first binding partner, and compounds of Formula VI as a second binding partner can also be generated.

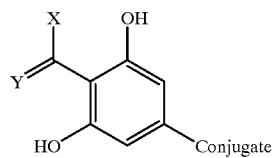

VI

Compounds of Formula VI and methods for their preparation are disclosed in U.S. Pat. Nos. 5,777,148 and 5,837,878, as well as copending applications: U.S. patent application Ser. No. 08/956,194, filed Oct. 22, 1997; and U.S. patent application Ser. No. 08/956,196, filed Oct. 22, 1997, which are incorporated herein by reference. The bioconjugates thus produced can be represented by Formula VII as follows:

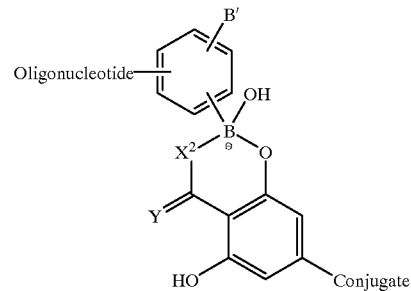

Bioconjugates of Formulae VI and VII can be prepared in buffered aqueous solution or organic solvents. The bioconjugate is formed within a few minutes over a range of temperatures of from about 4° C. to about 70° C. The stability of the bioconjugate in aqueous solution at a given pH and temperature is significantly influenced by groups X$^2$ and Y. For example, bioconjugates of Formula VI, wherein X is NOH and Y is O, are stable in aqueous solutions of approximate pH greater than 4.5 and less than 12.5. However, bioconjugates of Formula VII, wherein X is NOH and Y is O, are stable in aqueous solutions of approximate pH greater than 2.5 and less than 12.5. Consequently, bioconjugates of Formula VII are preferred when working in buffered aqueous solutions at low pH.

The bioconjugation reaction (boronic acid complexation) between each binding partner is insensitive to significant variations in ionic strength, the presence of organic solvents, the presence of detergents, and the presence of chaotropic agents (protein denaturants), which are incompatible with prior art indirect labeling systems wherein the structure of a biological macromolecule must be maintained to preserve requisite binding properties. In most instances, the constraints governing the formation of bioconjugates, by the system herein described, are limited to those imposed by the conditions required to maintain viability (native conformation) of the bioactive species.

The invention will be described in greater detail by way of specific examples. The following examples are offered for illustrative purposes, and are not intended to limit the invention in any manner. Those of skill in the art will readily recognize a variety of noncritical parameters that can be changed and modified to yield essentially the same results.

V. EXAMPLES

Example 1

This example illustrates the preparation of 1-O-(4,4'-Dimethoxytrityl)-8-N-[4-dihydroxyboryl(benzopinacol cyclic ester)-benzoyl)]amino-1,3-octanediol 3-O-(2-cyanoethyl)-N,N-diisopropylaminop phosphoramidite.

C. Synthesis of Methyl 8-[N-(benzyloxycarbonyl)amino]-3-oxooctanoate

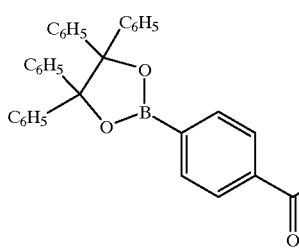 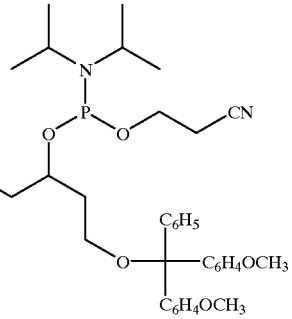

A. Synthesis of 4-dihydroxyboryl(benzopinacol cyclic ester) benzoic acid

4-Carboxyphenylboronic acid (10.0 g, 60.2 mmoles) was dissolved in hot, anhydrous 1,4-dioxane (150 mL), treated with a small quantity of activated charcoal, and filtered through a 0.5 um glass fiber filter while still hot. The filtrate was heated to reflux, and benzopinacol (22.1 g, 60.3 mmoles) was added. The solution was refluxed one hour, then cooled to room temperature. The solvent was then removed on a rotary evaporator to give a white solid, which was crystallized from ethyl ether/hexanes at −20° C. overnight. The solid was filtered and dried in vacuo to afford 23.3 g (78% yield) of product. The purity of the product was confirmed by $^1H$ and $^{13}C$ nuclear magnetic resonance (NMR) spectrometry as well as high performance liquid chromatography (HPLC).

$^1H$ NMR (300 MHz, DMSO-$d_6$): δ 13.23 (broad singlet, 1H, $CO_2H$), 8.19 (doublet, 2H, ArH[benzoic acid]), 8.13 (doublet, 2H, ArH), 7.10 (multiplet, 20H, ArH [benzopinacol]). $^{13}C$ NMR (75 MHz, DMSO-$d_6$): δ 167.4, 141.9, 135.4, 129.2, 128.2, 127.6, 127.4, 126.2, 96.3.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=14.9±0.1 minutes.

B. Synthesis of 4-dihydroxyboryl(benzopinacol cyclic ester) benzoic Acid NHS Ester 4-dihydroxyboryl(benzopinacol cyclic ester)benzoic acid (17.4 g, 35.0 mmoles) was dissolved in anhydrous tetrahydrofuran (100 mL). N-hydroxysuccinimide (4.0 g, 34.8 mmoles) was added, followed by 1,3-dicyclohexylcarbodiimide (7.2 g, 34.6 mmoles). The reaction was stirred overnight at room temperature, during which time a white precipitate of 1,3-dicyclohexylurea formed. The solid was removed by filtration and washed with a little tetrahydrofuran. The combined filtrates were evaporated to dryness on a rotary evaporator to give an off-white solid. The solid was dissolved in tetrahydrofuran (100 mL), the solution was filtered, and hexanes (300 mL) were added. Crystallization was allowed to occur overnight at −20° C. The solid was filtered and dried in vacuo to afford 18.4 g (89% yield) of product. The purity of the product was confirmed by $^1H$ and $^{13}C$ NMR.

$^1H$ NMR (300 MHz, DMSO-$d_6$): δ 8.31 (doublet, 2H, ArH[benzoic acid]), 8.25 (doublet, 2H, ArH[benzoic acid]), 7.15 (multiplet, 20H, ArH[benzopinacol]), 2.91 (singlet, 4H, $CH_2$). $^{13}C$ NMR (75 MHz, DMSO-$d_6$): δ 170.4, 161.9, 141.7, 136.0, 129.7, 128.2, 127.6, 127.4, 126.2, 96.5, 25.5.

6-[N-(Benzyloxycarbonyl)amino]hexanoic acid (25.0 g, 94.0 mmoles) and 2,2-dimethyl-1,3-dioxane-4,6-dione (13.6 g, 94.0 mmoles) were dissolved in anhydrous dichloromethane (500 mL). Triethylamine (35 mL, 255 mmoles) was added, and the reaction mixture was stirred at room temperature under dry nitrogen. Diethylcyano-phosphonate (15.4 mL, 94.0 mmoles) was added, and the solution rapidly turns yellow. After stirring overnight, the solution was carefully washed with 1 M aqueous hydrochloric acid (200 mL, twice), water (200 mL, thrice) and saturated aqueous sodium chloride (200 mL, once). The solution was dried over anhydrous magnesium sulfate, filtered, and concentrated to a thick orange syrup on a rotary evaporator. This material was dissolved in absolute methanol (500 mL) and refluxed under dry nitrogen for four hours. The solution was cooled, and the solvent removed on a rotary evaporator. The residue was dissolved in ethyl acetate:hexanes (1:1, v/v, 50 mL) and 10 mL aliquots were purified by preparative HPLC (Waters PrepLC 2000 system) on a column of Porasil silica (47 mm×300 mm; Waters). The flow rate was 50 mL/minute. The following step gradient was used: 50:50 (v/v) ethyl acetate:hexanes for 22 minutes, then 100% ethyl acetate for 18 minutes, then 100% methanol for 20 minutes. The eluent was monitored by absorbance at 270 nm; the product elutes in the first major peak. Product fractions were pooled and evaporated to dryness on a rotary evaporator to yield a clear, pale yellow syrup which solidifies on storage at 4° C. to afford 27.7 g (92% yield) of product. The purity of the product was confirmed by $^1H$ and $^{13}C$ NMR as well as by HPLC.

$^1H$ NMR (300 MHz, DMSO-$d_6$): δ 7.33 (multiplet, 5H, ArH), 7.23 (triplet, 1H, NH), 5.00 (singlet, 2H, $ArCH_2O$), 3.60 (singlet, 3H, $OCH_3$), 3.58 (singlet, 2H, [C=O]$CH_2$ [C=O]), 2.97 (quartet, 2H, $NHCH_2CH_2$), 2.49 (triplet, 2H, $CH_2CH_2$[C=O]). 1.40 (multiplet, 4H, $NHCH_2CH_2$ and $CH_2CH_2$[C=O]), 1.20 (multiplet, 2H, $CH_2CH_2CH_2$). $^{13}C$ NMR (75 MHz, DMSO-$d_6$): δ 203.6, 168.0, 156.3, 137.5, 128.4, 127.8, 65.2, 51.7, 48.5, 42.1, 40.1, 29.2, 25.6, 22.5. HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): RT=13.1±0.1 minutes.

C. Synthesis of Methyl 8-[N-(benzyloxycarbonyl)amino]-1,3-octanediol

Methyl 8-[N-(benzyloxycarbonyl)amino]-3-oxooctanoate (26.0 g, 80.9 mmoles) was dissolved in anhydrous tetrahydrofuran (125 mL). This solution was added slowly dropwise to a chilled (ice bath) solution of lithium borohydride (6.1 g, 279.8 mmoles) in anhydrous tetrahydrofuran (250 mL) under dry nitrogen. After the addition was completed, the reaction mixture was allowed to warm to room temperature and was stirred overnight. The mixture was then chilled in an ice bath, and 1 M aqueous hydrochloric acid (300 mL) was added slowly dropwise. When the addition was complete and the foaming ceased, the mixture was concentrated on a rotary evaporator to remove most of the tetrahydrofuran. Chloroform was added (250 mL) to the residue (water plus product), the mixture was shaken well, and the layers were separated. The aqueous layer was extracted with additional chloroform (250 mL). The chloroform extracts were washed with saturated aqueous sodium chloride (100 mL, once), dried over anhydrous sodium sulfate, and filtered. The filtrate was evaporated to dryness to give a thick, clear, colorless syrup. The syrup was co-evaporated with methanol (100 mL, 5 times), and the residue was crystallized from ethyl ether and hexanes, overnight at −20° C. The white solid was filtered and dried in vacuo to afford 23.5 g (98% yield) of product. The purity of the product was confirmed by $^1$H and $^{13}$C NMR as well as by HPLC. $^1$H NMR (300 MHz, DMSO-$d_6$): δ 7.33 (multiplet, 5H, ArH), 7.22 (triplet, 1H, NH), 5.00 (singlet, 2H, ArCH$_2$O), 4.33 (triplet, 1H, CH$_2$OH), 4.29 (doublet, 1H, CHOH), 3.50 (multiplet, 3H, CH[OH]CH$_2$CH$_2$OH), 2.98 (doublet of triplets, 2H, NHCH$_2$CH$_2$), 1.52–1.23 (multiplet, 10H, NHCH$_2$CH$_2$CH$_2$CH$_2$CH$_2$CH[OH]CH$_2$CH$_2$OH). $^{13}$C NMR (75 MHz, DMSO-$d_6$): δ 156.4, 137.6, 128.5, 127.9, 67.4, 65.2, 58.4, 40.4, 40.2, 37.5, 29.5, 26.4, 25.0. HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=11.0±0.1 minutes.

D. Synthesis of 1-O-(4,4'-dimethoxytrityl)-8-N-(benzyloxycarbonyl)amino-1,3-octanediol Methyl 8-[N-(benzyloxycarbonyl)amino]-1,3-octanediol (8.3 g, 28.0 mmoles) was co-evaporated with anhydrous pyridine (50 mL, once). The resulting syrup was dissolved in anhydrous pyridine (50 mL) and 4,4'-dimethoxytrityl chloride (10.0 g, 29.5 mmoles) was added. The orange solution was stirred overnight at room temperature in the absence of moisture. Methanol (10 mL) was then added, and the solution was stirred an additional hour at room temperature. t-Butyl methyl ether (200 nL) was added, the mixture shaken well, and the suspension allowed to sit for two hours at −20° C. The mixture was filtered, the solid washed with t-butyl methyl ether (100 mL) and the combined filtrates were concentrated to a thick yellow syrup on a rotary evaporator. The syrup was dissolved in ethyl acetate (20 mL) and hexanes (20 mL) plus triethylamine (1 mL), and 5 mL aliquots of this solution were purified by preparative HPLC (Waters PrepLC 2000 system) on a column of Porasil silica (47 mm×300 mm; Waters). The flow rate was 50 mL/minute of 39:60:1 (v/v/v) ethyl acetate:hexanes:triethylamine. The eluent was monitored by absorbance at 280 nm. Product fractions were pooled and evaporated to dryness on a rotary evaporator to yield a clear, pale yellow syrup. The syrup was further dried in vacuo over potassium hydroxide pellets to afford 12.9 g (77% yield) of product. The purity of the product was confirmed by $^1$H and $^{13}$C NMR as well as by HPLC. $^1$H NMR (300 MHz, acetonitrile-$d_3$): δ 7.45–7.27 (multiplet, 14H, ArH [DMT, Cbz]), 7.22 (triplet, 1H, NH), 6.86 (doublet, 4H, ArH[DMT]), 5.62 (broad singlet, 1H, CHOH), 5.04 (singlet, 2H, ArCH$_2$O), 3.75 (singlet, 6H, Ar—OCH$_3$), 3.63 (doublet, 1H, CHOH), 3.20–3.00 (multiplet, 4H, NHCH$_2$CH$_2$ and CH$_2$CH$_2$O-DMT), 1.72–1.23 (multiplet, 10H, NHCH$_2$CH$_2$CH$_2$—CH$_2$CH$_2$CH[OH]—CH$_2$CH$_2$O-DMT). $^{13}$C NMR (75 MHz, chloroform-d): δ 158.9, 156.8, 145.1, 137.0, 136.3, 130.3, 128.8, 128.3, 128.2, 127.1, 113.5, 87.0, 71.5, 66.7, 62.7, 55.4, 41.2, 37.4, 36.9, 30.1, 26.8, 25.3. HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): RT=17.2±0.1 minutes.

E. Synthesis of 1-O-(4,4'-dimethoxytrityl)-8-amino-1,3-octanediol

1-O-(4,4'-Dimethoxytrityl)-8-N-(benzyloxycarbonyl)amino-1,3-octanediol (12.9 g, 21.6 mmoles) was dissolved in methanol (250 mL). The solution was placed in a one liter Parr hydrogenation vessel, and the solution was purged with nitrogen for five minutes. Palladium on carbon catalyst (1.0 g, 10% Pd/C) slurried in ethyl acetate (20 mL) was added, and the vessel was affixed to a Parr shaker. The vessel was again purged with nitrogen, evacuated, and hydrogen was introduced to a pressure of 35 psi. The vessel was shaken for six hours at room temperature, then evacuated, filled with nitrogen and removed from the shaker. The contents were filtered through a 0.5 μm glass fiber filter, and the filtrate was evaporated to dryness on a rotary evaporator to yield a clear, colorless syrup. The syrup was further dried in vacuo over potassium hydroxide to afford 10.1 g (100% yield) of product. The purity of the product was confirmed by $^1$H and $^{13}$C NMR as well as by HPLC. $^1$H NMR (300 MHz, DMSO-$d_6$): δ 7.38–7.16 (multiplet, 9H, ArH), 6.86 (doublet, 4H, ArH), 3.71 (singlet, 6H, Ar—OCH$_3$), 3.63 (multiplet, 4H, CHOH and CH$_2$NH$_2$), 3.04 (triplet, 2H, NH$_2$CH$_2$CH$_2$), 2.53 (triplet, 2H, CH$_2$CH$_2$O-DMT), 161–1.17 (multiplet, 10H, NH$_2$CH$_2$CH$_2$—CH$_2$CH$_2$CH$_2$CH[OH]CH$_2$CH$_2$O-DMT). $^{13}$C NMR (75 MHz, DMSO-$d_6$): δ 158.2, 145.6, 136.4, 128.9, 129.1, 127.9, 126.7, 113.2, 85.4, 67.3, 60.7, 55.0, 41.1, 37.5, 32.3, 26.5, 25.1. HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=12.7±0.1 minutes.

F. 1-O-(4,4'-Dimethoxytrityl)-8-N-[(4-dihydroxyboryl (benzopinacol cyclic ester)benzoyl]amino-1,3-octanediol 1-O-(4,4'-Dimethoxytrityl)-8-amino-1,3-octanediol (10.0 g, 21.6 mmoles) was dissolved in anhydrous tetrahydrofuran (100 mL) and 4-dihydroxyboryl(benzopinacol cyclic ester) benzoic acid N-hydroxysuccinimide ester (12.8 g, 21.6 mmoles) was added. The clear solution was stirred overnight at room temperature under dry nitrogen. The reaction mixture was then concentrated to a thick syrup on a rotary evaporator. The residue was dissolved in ethyl acetate (100 mL) containing triethylamine (10 mL), and the solution was chilled for several hours at 4° C. The cold mixture was filtered to remove some precipitated solid and the filtrate was concentrated to a thick syrup on a rotary evaporator. The residue was dissolved in ethyl acetate (25 mL) and hexanes (25 mL) containing triethylamine (1 mL), and 5 mL aliquots of this solution were purified by preparative HPLC (Waters PrepLC 2000 system) on a column of Porasil silica (47×300 mm; Waters). The flow rate was 50 mL/minute of 39:60:1 (v/v/v) ethyl acetate:hexanes:triethylamine. The eluent was monitored by absorbance at 280 nm. Product fractions were pooled and evaporated to dryness on a rotary evaporator to yield a clear, pale brown syrup. The syrup was further dried in vacuo over potassium hydroxide pellets to afford 14.9 g (73% yield) of a pale tan, glassy foam. The purity of the product was confirmed by $^1$H and $^{13}$C NMR as well as by both gradient and isocratic HPLC. $^1$H NMR (300 MHz, DMSO-$d_6$): δ 8.61 (triplet, 1H, NH), 8.14 (doublet, 2H, ArH[PBA]), 8.00 (doublet, 2H, ArH[PBA]), 7.39–7.09 (multiplet, 30H, ArH [DMT, benzopinacol]), 6.86 (doublet, 4H, ArH[DMT]), 4.27 (doublet, 1H, CHOH), 3.70 (singlet, 6H, Ar—OCH$_3$), 3.57 (broad singlet, 1H, CHOH), 3.29 (doublet of triplets, 2H, NHCH$_2$CH$_2$), 3.07 (triplet, 2H, CH$_2$CH$_2$O-DMT), 1.70–1.23 (multiplet, 10H, NHCH$_2$CH$_2$CH$_2$CH$_2$CH$_2$CH—[OH]CH$_2$CH$_2$O-DMT). $^{13}$C NMR (75 MHz, DMSO-$d_6$): δ 166.0, 158.1, 145.4, 141.9, 138.4, 136.3, 135.1, 129.7, 128.1, 127.8, 127.5, 127.2, 127.0, 126.5, 113.1, 96.1, 85.3, 67.2, 60.5, 55.9, 38.1, 37.4, 29.1, 26.6, 24.9. HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=19.4±0.1 minutes. HPLC (reverse phase, 4.6×100 mm C4 column, flow rate 1.0 mL/minute, isocratic elution using 7% 0.1 M triethylammonium acetate, pH 6.5:93% acetonitrile): Retention time= 6.2±0.1 minutes.

G. Synthesis of 1-O-(4,4'-Dimethoxytrityl)-8-N-[(4-dihydroxyboryl(benzopinacol cyclic ester)-benzoyl]-amino-1,3-octanediol 3-O-(2-cyanoethyl)-N,N-diisopropylamino Phosphoramidite 1-O-(4,4'-Dimethoxytrityl)-8-N-[(4-dihydroxyboryl(benzopinacol cyclic ester)benzoyl]-amino-1,3-octanediol (3.5 g, 3.7 mmoles) was dissolved in anhydrous dichloromethane (50 mL, filtered through basic alumina). N,N-diisopropylethylamine (2.6 mL, 14.9 mmoles) was added, and the solution was stirred under dry nitrogen at room temperature. 2-Cyanoethyl-N,N-diisopropyl-amino chlorophosphine (1.2 mL, 5.4 mmoles) was added dropwise, and the solution was stirred for one hour. The reaction mixture was then concentrated to about 20 mL on a rotary evaporator, and ethyl acetate (150 mL, pre-washed with 100 mL of saturated aqueous sodium bicarbonate) was added. The organic solution was washed with saturated aqueous sodium bicarbonate (50 mL, once) then saturated aqueous sodium chloride (50 mL, once), dried over anhydrous magnesium sulfate, and filtered. The filtrate was evaporated to dryness on a rotary evaporator to give a pale yellow syrup. This material was dissolved in ethyl acetate (25 mL) and hexanes (25 mL) containing triethylamine (1 mL). Five mL aliquots of this solution were purified by preparative HPLC on a column of Porasil silica (40 mm×100 mm; Waters). The flow rate was 50 mL/minute of 19:80:1 (v/v/v) ethyl acetate:hexanes:triethylamine. The eluent was monitored by absorbance at 270 nm; the product elutes in the major peak. Product fractions were pooled and evaporated to dryness on a rotary evaporator to yield a clear, colorless glassy foam, which was further dried in vacuo over anhydrous potassium carbonate to afford 2.7 g (78% yield) of product. The purity of the product was confirmed by $^1$H NMR and by HPLC. $^1$H NMR (300 MHz, acetonitrile-$d_3$): δ 8.14 (doublet, 2H, ArH[PBA]), 7.89 (doublet, 2H, ArH[PBA]), 7.43–7.08 (multiplet, 31H, ArH [DMT, benzopinacol]and NH), 6.86–6.82 (two doublets, 4H, ArH[DMT]), 3.95 (multiplet, 1H, CHO—P), 3.74–3.734 (two singlets, 6H, Ar—OCH$_3$), 3.50 (multiplet, 4H, OCH$_2$CH$_2$CN and NCH(CH$_3$)$_2$), 3.34 (multiplet, 2H NHCH$_2$CH$_2$), 3.12 (multiplet, 2H, CH$_2$CH$_2$O-DMT), 2.58–2.46 (doublet of triplets, 2H, OCH$_2$CH$_2$CN), 1.80–1.30 (multiplet, 10H, NHCH$_2$CH$_2$CH$_2$CH$_2$CH$_2$CH[OH]CH$_2$CH$_2$O-DMT), 1.12–1.01 (two doublets of doublets, 12H, NCH(CH$_3$)$_2$). Note that the $^1$H NMR spectrum was complicated due to the presence of partially resolved diastereomers. HPLC (reverse phase, 4.6×100 mm C4 column, flow rate 1.0 mL/minute, isocratic elution using 7% 0.1 M triethylammonium acetate, pH 6.5:93% acetonitrile): Retention time=11.7 and 12.8±0.1 minutes (diastereomers).

Example 2

This example illustrates the preparation of 1-O-(4,4'-Dimethoxytrityl)-3-N-[(4-dihydroxyboryl(benzopinacol cyclic ester)-benzoyl)-β-alanyl)]amino-1,2-propanediol 3-O-(2-cyanoethyl)-N,N-diisopropylamino phosphoramidite.

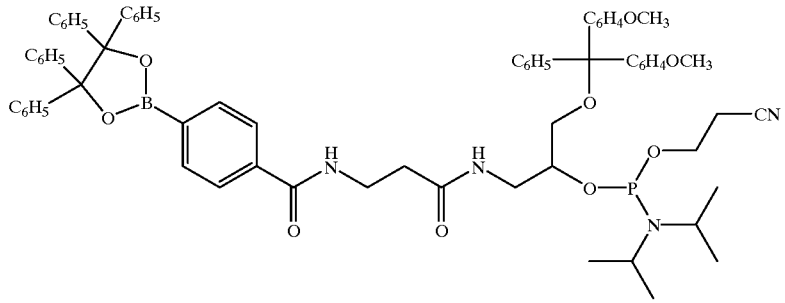

A. Synthesis of 4-dihydroxyboryl(benzopinacol cyclic ester) benzoic Acid

Figure 4:
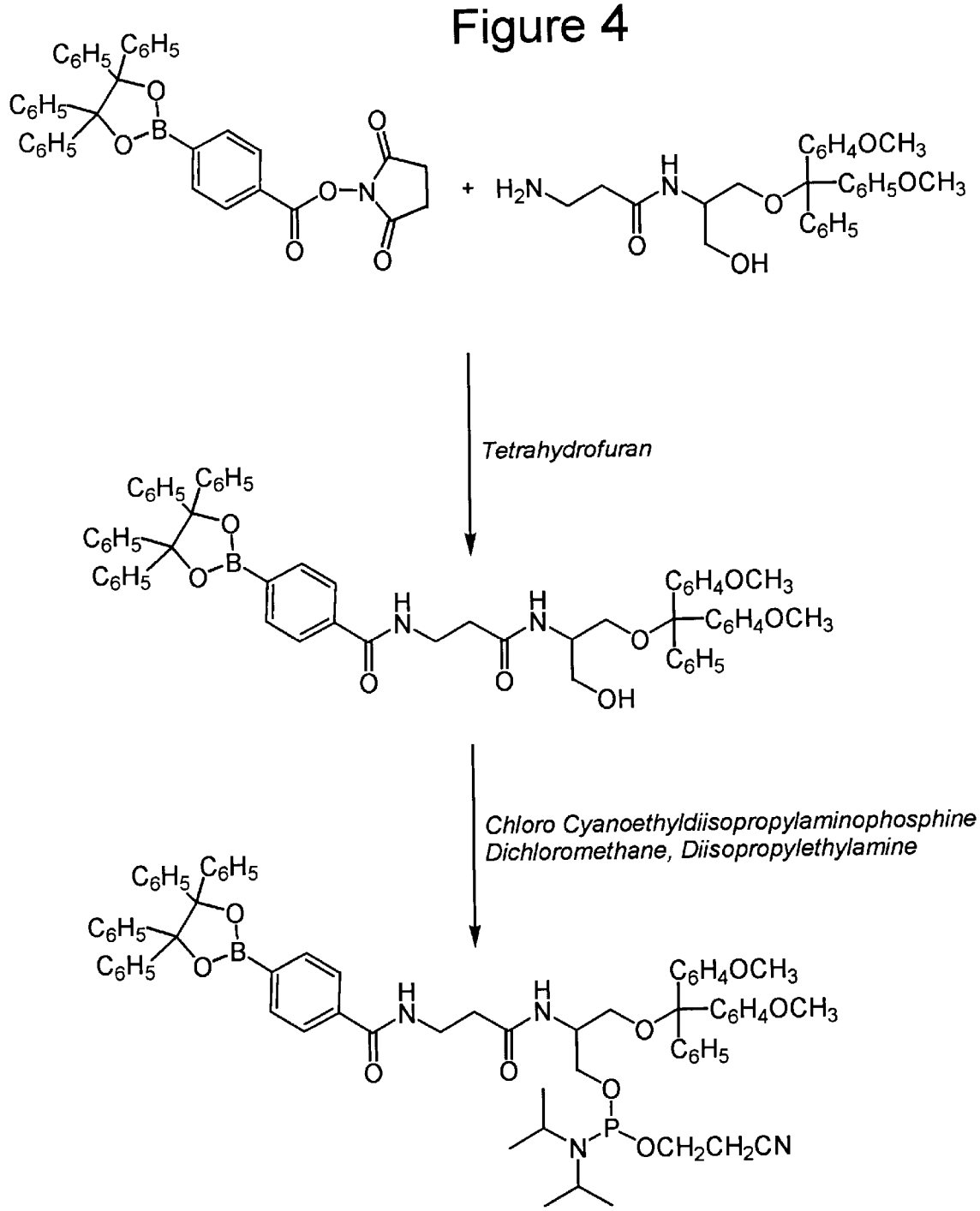
FIG. 4 summarizes a synthetic method to prepare 1-O-(4,4'-dimethoxytrityl)-2-N-[(4-dihydroxy-boryl (benzopinacol cyclic ester)benzoyl)-β-alanyl]serinol 3-O-(2-cyanoethyl)-N,N-diisopropyl-amino phosphoramidite, a compound of the present invention.
Figure 5:
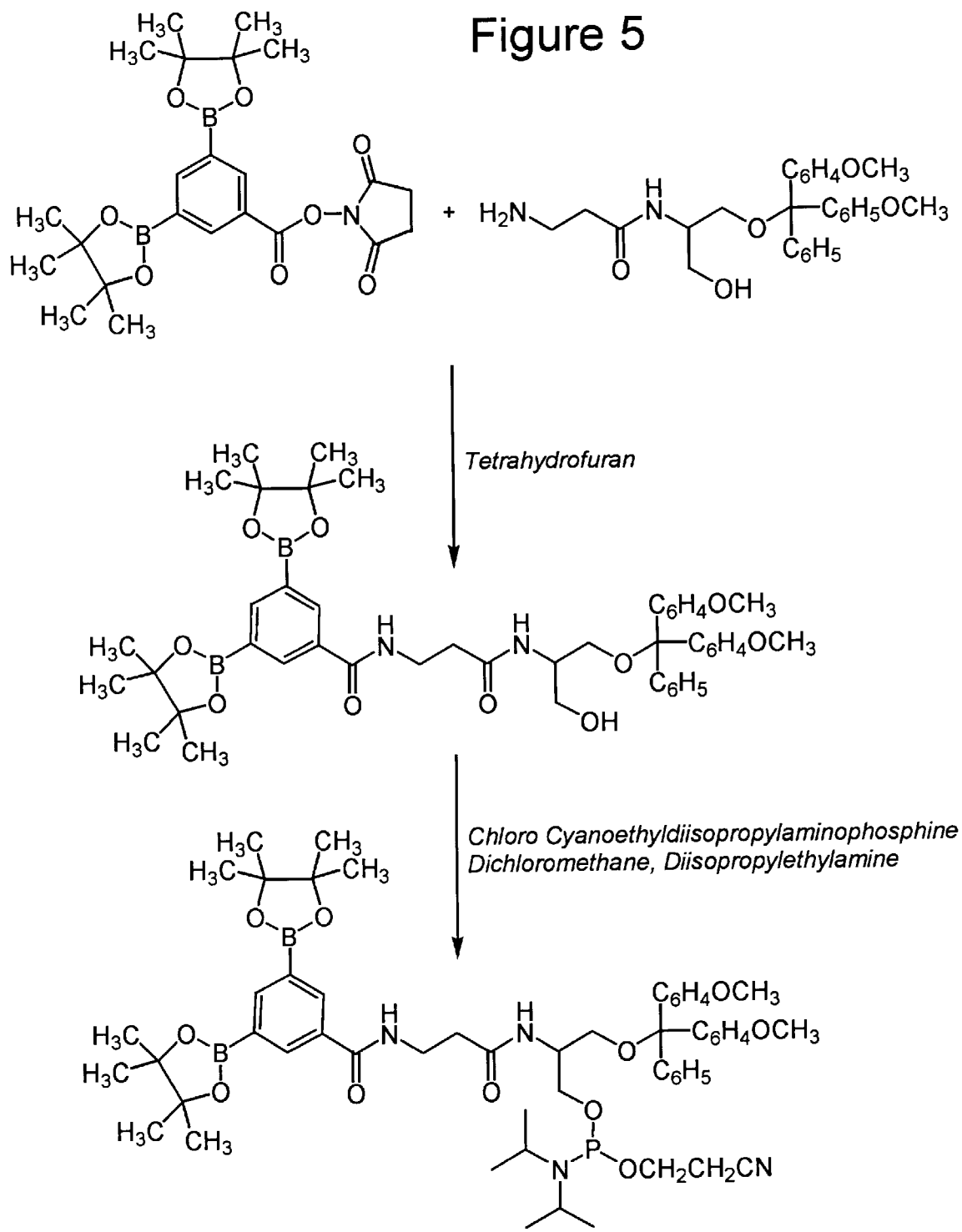
FIG. 5 summarizes a synthetic method to prepare 1-O-(4,4'-dimethoxytrityl)-2-N-[(3,5-bis-di-hydroxyboryl (pinacol cyclic ester) benzoyl)-β-alanyl] serinol 3-O-(2-cyanoethyl)-N,N-diiso-propylamino phosphoramidite, a compound of the present invention.

With reference to FIGS. 4 and 5, 4-Carboxyphenylboronic acid (10.0 g, 60.2 mmoles) was dissolved in hot, anhydrous 1,4-dioxane (150 mL), treated with a small quantity of activated charcoal, and filtered through a 0.5 μm glass fiber filter while still hot. The filtrate was heated to reflux, and benzopinacol (22.1 g, 60.3 mmoles) was added. The solution was refluxed one hour, then cooled to room temperature. The solvent was then removed on a rotary evaporator to give a white solid, which was crystallized from ethyl ether/hexanes at −20° C. overnight. The solid was filtered and dried in vacuo to afford 23.3 g (78% yield) of product. The purity of the product was confirmed by $^1$H and $^{13}$C NMR as well as by HPLC.

$^1$H NMR (300 MHz, DMSO-$d_6$): δ 13.23 (broad singlet, 1H, CO$_2$H), 8.19 (doublet, 2H, ArH[benzoic acid]), 8.13 (doublet, 2H, ArH), 7.10 (multiplet, 20H, ArH [benzopinacol]). $^{13}$C NMR (75 MHz, DMSO-$d_6$): δ 167.4, 141.9, 135.4, 129.2, 128.2, 127.6, 127.4, 126.2, 96.3.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=14.9±0.1 minutes.

B. Synthesis of 4-dihydroxyboryl(benzopinacol cyclic ester) benzoic Acid NHS Ester 4-dihydroxyboryl(benzopinacol cyclic ester)benzoic acid (17.4 g, 35.0 mmoles) was dissolved in anhydrous tetrahydrofuran (100 mL). N-hydroxysuccinimide (4.0 g, 34.8 mmoles) was added, followed by 1,3-dicyclohexylcarbodiimide (7.2 g, 34.6 mmoles). The reaction was stirred overnight at room temperature, during which time a white precipitate of 1,3-dicyclohexylurea forms. The solid was removed by filtration and washed with a little tetrahydrofuran. The combined filtrates were evaporated to dryness on a rotary evaporator to give an off-white solid. The solid was dissolved in tetrahydrofuran (100 mL), the solution was filtered, and hexanes (300 mL) were added. Crystallization was allowed to occur overnight at −20° C. The solid was filtered and dried in vacuo to afford 18.4 g (89% yield) of product. The purity of the product was confirmed by $^1$H and $^{13}$C NMR.

$^1$H NMR (300 MHz, DMSO-$d_6$): δ 8.31 (doublet, 2H, ArH[benzoic acid]), 8.25 (doublet, 2H, ArH[benzoic acid]), 7.15 (multiplet, 20H, ArH[benzopinacol]), 2.91 (singlet, 4H, CH$_2$). $^{13}$C NMR (75 MHz, DMSO-$d_6$): δ 170.4, 161.9, 141.7, 136.0, 129.7, 128.2, 127.6, 127.4, 126.2, 96.5, 25.5.

C. Synthesis of 3-(N-benzyloxycarbonyl-β-alanyl)amino-1,2-propanediol

N-Benzyloxycarbonyl-β-alanine N-hydroxysuccinimide ester (16.0 g, 50.0 mmoles) was dissolved (with gentle warming) in 50 mL of 2-propanol, and 3-amino-1,2-propanediol (4.6 g, 50.4 mmoles) was added. The mixture stirred at room temperature overnight. A white precipitate formed. The solvent was then removed on a rotary evaporator to give a white solid, which was dissolved in water (200 mL). Anion exchange resin (AG1-X8 [OH form], 50 g moist weight; Bio-Rad) was added, and the slurry was stirred for one hour. The resin was removed by filtration, and washed with water (100 mL, once) and methanol (100 mL, twice). The combined filtrates were evaporated to dryness on a rotary evaporator to give a white solid. The solid was co-evaporated with toluene (100 mL, once), then dried well in vacuo to afford 14.1 g (96% yield) of product. The purity of the product was confirmed by $^1$H and $^{13}$C NMR as well as by HPLC.

$^1$H NMR (300 MHz, DMSO-$d_6$): δ 7.85 (triplet, 1H, NH[aminopropanediol]), 7.37–7.26 (multiplet, 5H, ArH), 7.21 (triplet, 1H, NH[β-alanine]), 4.99 (singlet, 2H, ArCH$_2$O), 4.64 (broad singlet, 2H, OH), 3.48 (pentet, 1H, CH$_2$CH[OH]CH$_2$OH), 3.27 (doublet of doublets, 2H, CH$_2$CH[OH]CH$_2$OH), 3.18 (quartet, 2H, NHCH$_2$CH$_2$), 3.08 (doublet of multiplets, 2H, CH$_2$CH[OH]CH$_2$OH), 2.28 (triplet, 2H, NHCH$_2$CH$_2$). $^{13}$C NMR (75 MHz, DMSO-$d_6$): δ 171.0, 156.3, 137.4, 128.5, 127.9, 70.5, 65.3, 63.8, 42.2, 37.2, 35.7.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=9.4±0.1 minutes.

D. Synthesis of 1-O-(4,4'-dimethoxytrityl)-3-(N-benzyloxycarbonyl-β-alanyl)amino-1,2-propanediol 3-(N-Benzyloxycarbonyl-β-alanyl)amino-1,2-propanediol (5.0 g, 16.9 mmoles) was dissolved in dry pyridine (50 mL) and 4,4'-dimethoxytrityl chloride (5.7 g, 16.9 mmoles) was added. The yellow solution was stirred overnight under dry nitrogen at room temperature. Methanol (10 mL) was then added and the solutions stirred and additional hour. The solvent was removed on a rotary evaporator at a bath temperature of <40° C. to give a thick yellow syrup. The syrup was partitioned between ethyl acetate (200 mL) and 5% (w/v) aqueous sodium carbonate (100 mL). The layers were separated, and the ethyl acetate layer was washed with saturated aqueous sodium chloride (150 mL, once). The ethyl acetate solution was dried over anhydrous magnesium sulfate, filtered, and concentrated to a yellow gum on a rotary evaporator. The gum was dissolved in ethyl acetate:hexanes (1:1 v/v, 30 mL) containing triethylamine (1 mL), filtered, and 5 mL aliquots of this solution were purified by preparative HPLC (Waters PrepLC 2000 system) on a column of Porasil silica (47×300 mm; Waters). The flow rate was 50 mL/minute. The following step gradient was used: 74:25:1 (v/v/v) ethyl acetate:hexanes:triethylamine for 10 minutes to elute some minor contaminants, then 94:5:1 (v/v/v) ethyl acetate:methanol:triethylamine for 20 minutes to elute the desired product. The eluent was monitored by absorbance at 270 nm. Product fractions were pooled and evaporated to dryness on a rotary evaporator to yield a clear, pale yellow syrup. The syrup was further dried in vacuo over potassium hydroxide pellets to afford 5.4 g (54% yield) of a crisp, glassy foam. The purity of the product was confirmed by $^1$H and $^{13}$C NMR as well as by HPLC.

$^1$H NMR (300 MHz, DMSO-$d_6$): δ 7.80 (triplet, 1H, NH[aminopropanediol), 7.41–7.18 (multiplet, 15H, ArH [DMT, Cbz] and NH[β-alanine]), 6.88 (doublet, 4H, ArH [DMT]), 5.00 (singlet, 2H, ArCH$_2$O), 4.97 (doublet, 1H, CH[OH]), 3.72 (singlet, 6H, ArOCH$_3$), 3.68 (multiplet, 1H, CH$_2$CH[OH]CH$_2$O-DMT), 3.19 (quartet, 2H, NHCH$_2$CH$_2$), 3.14 (doublet of multiplets, 2H, CH$_2$CH[OH]CH$_2$O-DMT), 2.85 (multiplet, 2H, CH$_2$CH[OH]CH$_2$O-DMT), 2.24 (triplet, 2H, NHCH$_2$CH$_2$). $^{13}$C NMR (75 MHz, DMSO-$d_6$): δ 170.5, 158.1, 156.0, 145.0, 137.2, 135.9, 129.7, 128.2, 127.8, 127.6, 127.5, 126.5, 113.1, 85.2, 68.7, 65.7, 65.1, 54.9, 42.6, 37.1, 35.5.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=15.3±0.1 minutes.

E. Synthesis of 1-O-(4,4'-dimethoxytrityl)-3-(β-alanyl)amino-1,2-propanediol

1-O-(4,4'-Dimethoxytrityl)-3-(N-benzyloxycarbonyl-β-alanyl)amino-1,2-propanediol (5.4 g, 9.0 mmoles) was dissolved in absolute methanol (150 mL). The solution was placed in a one liter Parr hydrogenation vessel, and the solution was purged with nitrogen for five minutes. Palladium on carbon catalyst (1.0 g, 10% Pd/C) slurried in ethyl acetate (20 mL) was added, and the vessel was affixed to a Parr shaker. The vessel was again purged with nitrogen, evacuated, and hydrogen was introduced to a pressure of 35 psi. The vessel was shaken for six hours at room temperature, then evacuated, filled with nitrogen and removed from the shaker. The contents were filtered through a 0.5 μm glass fiber filter, and the filtrate was evaporated to dryness on a rotary evaporator to yield a clear, colorless syrup. The syrup was further dried in vacuo over potassium hydroxide pellets to afford 4.0 g (96% yield) of a crisp, glassy foam. The purity of the product was confirmed by $^1$H and $^{13}$C NMR as well as by HPLC.

$^1$H NMR (300 MHz, DMSO-$d_6$): δ 7.86 (triplet, 1H, NH[aminopropanediol), 7.40–7.18 (multiplet, 9H, ArH), 6.87 (doublet, 4H, ArH), 3.72 (singlet, 6H, ArOCH$_3$), 3.68 (multiplet, 1H, CH$_2$CH[OH]CH$_2$O-DMT), 3.21 (doublet of multiplets, 2H, CH$_2$CH[OH]CH$_2$O-DMT), 3.10 (broad singlet, 3H, NH$_2$ and OH), 2.90 (multiplet, 2H, CH$_2$CH[OH] CH$_2$O-DMT), 2.68 (triplet, 2H, NH$_2$CH$_2$CH$_2$), 2.24 (triplet, 2H, $NH_2CH_2CH_2$). $^{13}C$ NMR (75 MHz, DMSO-$d_6$): δ 171.7, 158.1, 145.1, 136.0, 129.7, 127.8, 127.7, 126.5, 113.1, 85.2, 68.7, 65.7, 54.9, 42.5, 38.7, 38.1.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=11.9±0.1 minutes.

F. Synthesis of 1-O-(4,4'-Dimethoxytrityl)-3-N-[(4-dihydroxyboryl(benzopinacol cyclic ester)-benzoyl)-β-alanyl)]amino-1,2-propanediol 1-O-(4,4'-Dimethoxytrityl)-3-(β-alanyl)amino-1,2-propanediol (4.0 g, 8.6 mmoles) was dissolved in anhydrous dichloromethane (100 mL) under dry nitrogen. 4-dihydroxyboryl-(benzopinacol cyclic ester)benzoic acid N-hydroxysuccinimide ester (8.5 g, 14.4 mmoles) was added, and the solution turned light yellow. The reaction mixture was stirred at room temperature for six hours, then washed successively with saturated aqueous sodium bicarbonate (100 mL, once) then saturated aqueous sodium chloride (100 mL, once). The solution was dried over anhydrous magnesium sulfate, filtered and evaporated to a yellow syrup on a rotary evaporator. The syrup was dissolved in ethyl acetate (25 mL) containing triethylamine (1 mL), and 5 mL aliquots of this solution were purified by preparative HPLC (Waters PrepLC 2000 system) on a column of Porasil silica (47×300 mm; Waters). The flow rate was 50 mL/minute. The following step gradient was used: 99:1 (v/v/v) ethyl acetate:triethylamine for 10 minutes to elute some minor contaminants, then 79:20:1 (v/v/v) ethyl acetate:methanol:triethylamine for 20 minutes to elute the desired product. The eluent was monitored by absorbance at 270 nm. Product fractions were pooled and evaporated to dryness on a rotary evaporator to yield a clear, pale yellow syrup. The syrup was further dried in vacuo over potassium hydroxide pellets to afford 3.9 g (48% yield) of a crisp, glassy foam. The purity of the product was confirmed by $^1H$ and $^{13}C$ NMR as well as by both gradient and isocratic HPLC.

$^1H$ NMR (300 MHz, DMSO-$d_6$): δ 8.64 (triplet, 1H, NH[β-alanine]), 8.11 (doublet, 2H, ArH[PBA]), 7.97 (doublet, 2H, ArH[PBA]), 7.86 (triplet, 1H, NH[aminopropanediol]), 7.41–7.08 (multiplet, 30H, ArH [DMT, benzopinacol]), 6.86 (doublet, 4H, ArH[DMT]), 4.97 (doublet, 1H, $CH_2CH[OR]CH_2O$-DMT), 3.72 (singlet, 6H, Ar$OCH_3$), 3.70 (multiplet, 1H, $CH_2CH[OH]CH_2O$-DMT), 3.46 (quartet, 2H, $NHCH_2CH_2$), 3.16 (doublet of multiplets, 2H, $CH_2CH[OH]CH_2O$-DMT), 2.89 (multiplet, 2H, $CH_2CH[OH]CH_2O$-DMT), 2.38 (triplet, 2H, $NHCH_2CH_2$). $^{13}C$ NMR (75 MHz, DMSO-$d_6$): δ 170.8, 166.2, 158.3, 145.2, 142.0, 138.3, 136.1, 135.1, 129.9, 128.2, 128.0, 127.8, 127.5, 127.3, 127.1, 126.7, 113.3, 96.3, 85.4, 68.9, 65.9, 55.1, 42.9, 36.3, 35.3.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=18.7±0.1 minutes.

HPLC (reverse phase, 4.6×100 mm C4 column, flow rate 1.0 mL/minute, isocratic elution using 7% 0.1 M triethylammonium acetate, pH 6.5:93% acetonitrile): Retention time=2.5±0.1 minutes.

G. Synthesis of 1-O-(4,4'-Dimethoxytrityl)-3-N-[(4-dihydroxyboryl(benzopinacol cyclic ester)-benzoyl)-β-alanyl)]amino-1,2-propanediol 2-O-(2-cyanoethyl)-N,N-diisopropylamino Phosphoramidite 1-O-(4,4'-Dimethoxytrityl)-2-N-[(4-dihydroxyboryl (benzopinacol cyclic ester)benzoyl)-β-alanyl)]amino-1,2-propanediol (3.9 g, 4.1 mmoles) was dissolved in anhydrous dichloromethane (100 mL, filtered through basic alumina). N,N-diisopropylethylamine (3.6 mL, 20.7 mmoles) was added, and the solution was stirred under dry nitrogen at room temperature. 2-Cyanoethyl-N,N-diisopropylamino chlorophosphine (1.1 mL, 5.0 mmoles) was added dropwise, and the solution was stirred for one hour. The reaction mixture was then diluted with dichloromethane (100 mL) and washed with saturated aqueous sodium bicarbonate (50 mL, once) then saturated aqueous sodium chloride (50 mL, once), dried over anhydrous magnesium sulfate, and filtered. The filtrate was evaporated to dryness on a rotary evaporator to give a pale yellow glassy foam. This material was dissolved in ethyl acetate (15 mL) and hexanes (10 mL) containing triethylamine (1 mL). Five mL aliquots of this solution were purified by preparative HPLC (Waters PrepLC 2000 system) on a column of Porasil silica (40×100 mm; Waters). The flow rate was 50 mL/minute. The following step gradient was used: 50:49:1 (v/v/v) ethyl acetate:hexanes:triethylamine for 10 minutes, then 99:1 (v/v) ethyl acetate:triethylamine for 5 minutes, then 49:50:1 ethyl acetate:methanol:triethylamine for 5 minutes'. The eluent was monitored by absorbance at 270 nm; the product elutes with 99:1 (v/v) ethyl acetate:triethylamine. Product fractions were pooled and evaporated to dryness on a rotary evaporator to yield a clear, colorless syrup. The syrup was further dried in vacuo over potassium hydroxide pellets to afford 3.6 g (76% yield) of a crisp, glassy foam. The purity of the product was confirmed by $^1H$ and $^{31}P$ NMR as well as by HPLC.

$^1H$ NMR (300 MHz, DMSO-$d_6$): δ 8.65 (doublet of triplets, 1H, NH[β-alanine]), 8.15 (doublet, 2H, ArH[PBA]), 7.99 (doublet, 2H, ArH[PBA]), 7.84 (doublet of triplets, 1H, NH[aminopropanediol]), 7.43–7.10 (multiplet, 30H, ArH [DMT, benzopinacol]), 6.87 (doublet of doublets, 4H, ArH [DMT]), 4.06 (multiplet, 1H, CH), 3.71 (singlet, 6H, Ar—$OCH_3$), 3.80–3.35 (multiplet, 8H, $OCH_2CH_2CN$, NCH $(CH_3)_2$, $CHCH_2OP$ and $NHCH_2CH_2$), 3.18 (doublet of multiplets, 2H, $CH_2CH[OH]CH_2O$-DMT), 3.03 (doublet of multiplets, 2H, $CH_2CH[OH]CH_2O$-DMT), 2.69 (doublet of triplets, 2H, $OCH_2CH_2CN$), 2.40 (multiplet, 2H, $NHCH_2CH_2$), 1.02 (doublet of doublets, 12H, $NCH(CH_3)_2$). Note that the $^1H$ NMR spectrum was complicated due to the presence of partially resolved diastereomers. $^{31}P$ NMR (121 MHz, DMSO-$d_6$): δ 149.1, 148.4 (diastereomers).

HPLC (reverse phase, 4.6×100 mm C4 column, flow rate 1.0 mL/minute, isocratic elution using 7% 0.1 M triethylammonium acetate, pH 6.5:93% acetonitrile): Retention time=4.1 and 4.8±0.1 minutes (diastereomers).

Example 3

This example illustrates the synthesis of 1-O-(4,4'-Dimethoxytrityl)-2-N-[(4-dihydroxyboryl(benzopinacol cyclic ester)-benzoyl)-β-alanyl)]serinol 3-O-(2-cyanoethyl)-N,N-diisopropylamino phosphoramidite.

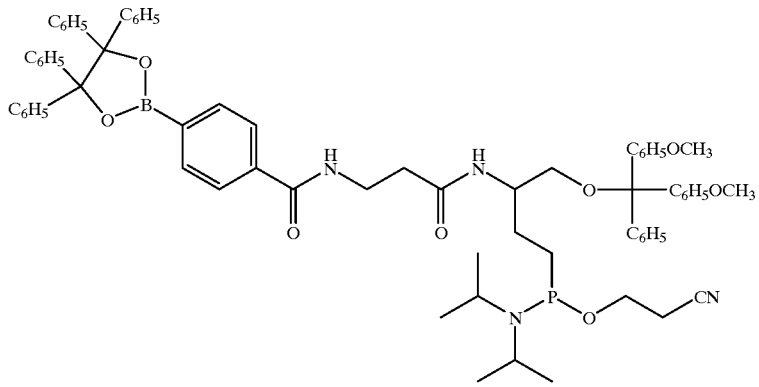

A. Synthesis of 4-Dihydroxyboryl(benzopinacol cyclic ester)benzoic Acid

Figure 6:
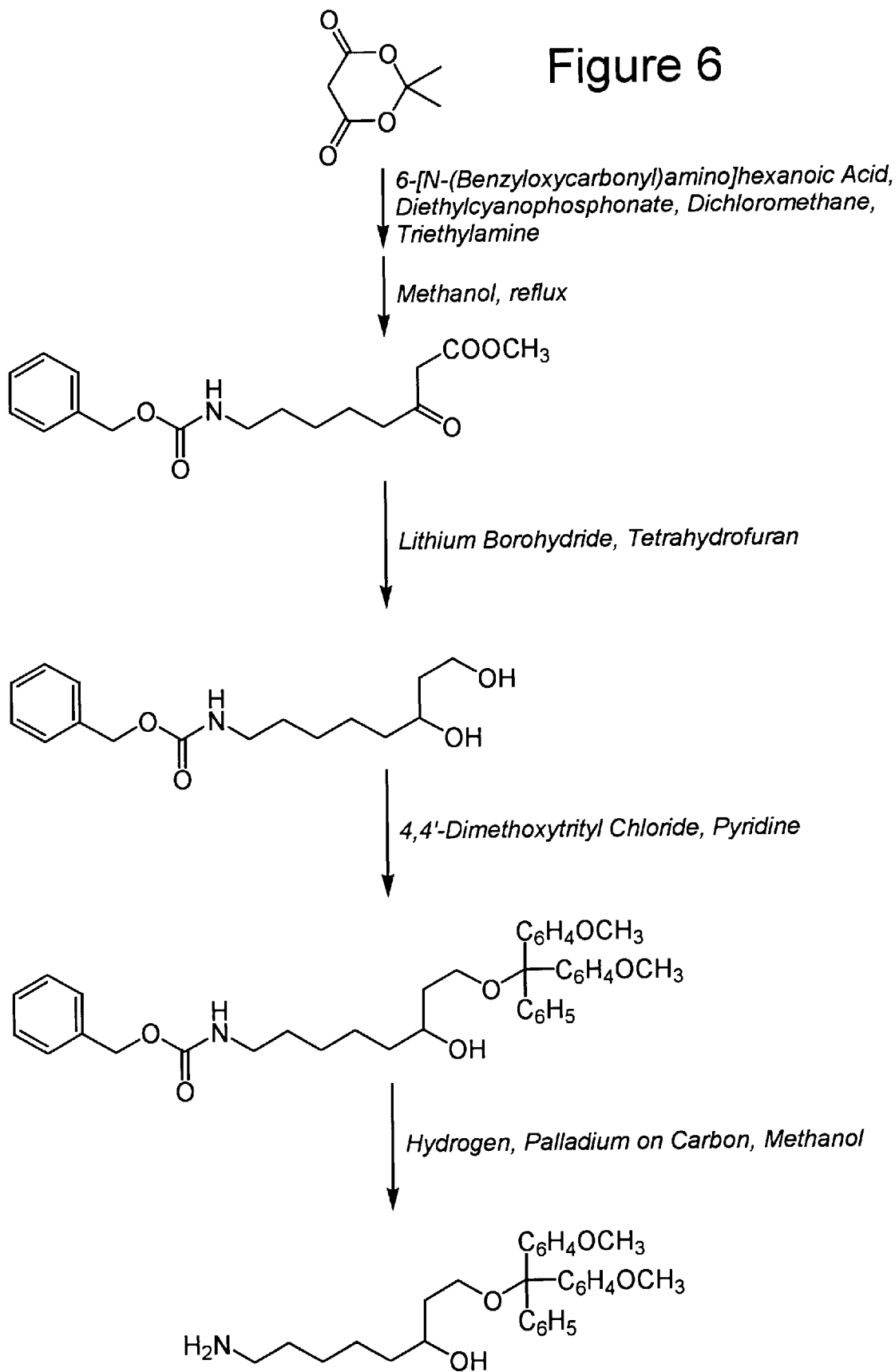
FIG. 6 summarizes a synthetic method to prepare 1-O-(4,4'-dimethoxytrityl)-8-amino-1,3-octane-diol, a compound of the present invention.
Figure 7:
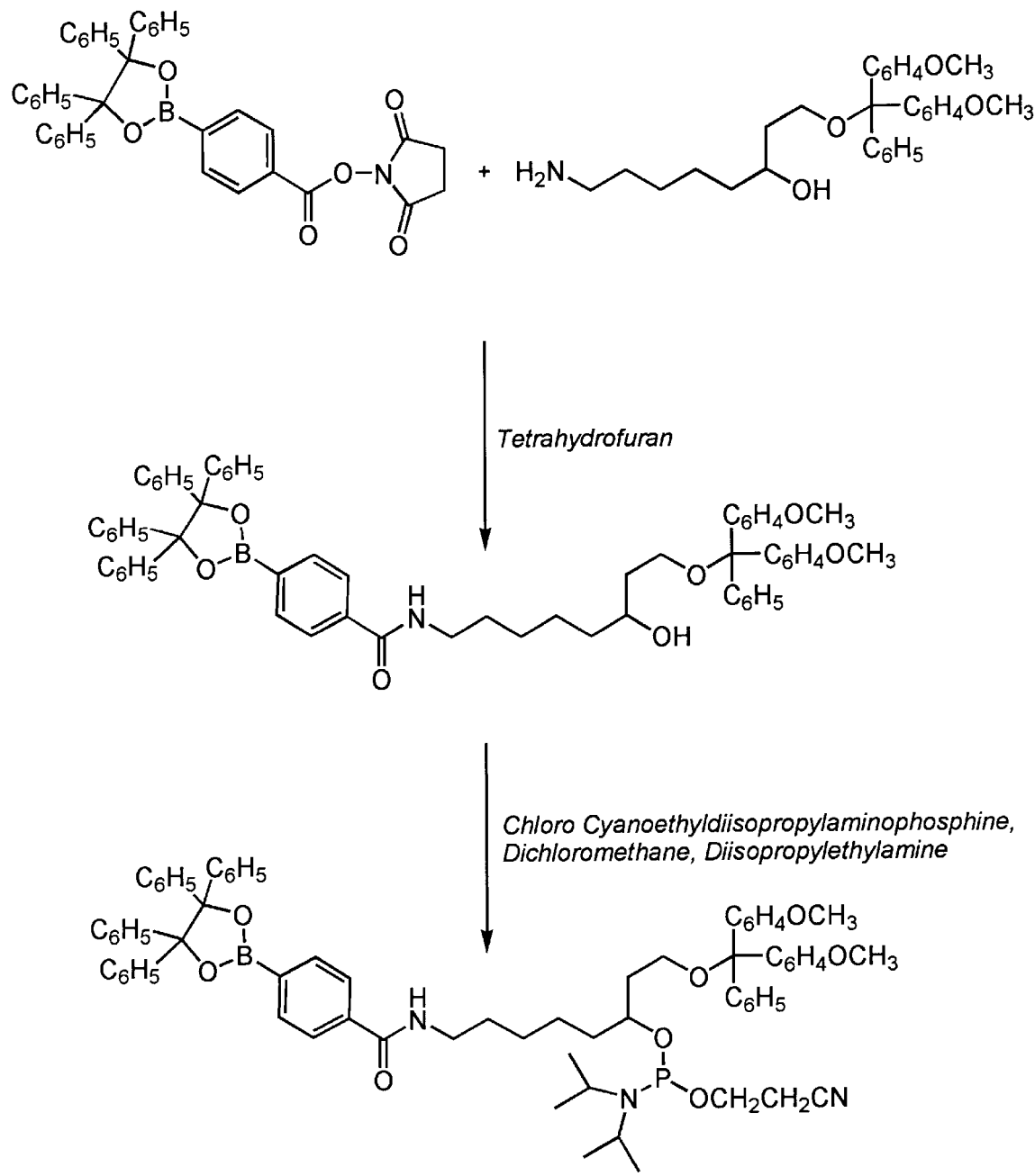
FIG. 7 summarizes a synthetic method to prepare 1-O-(4,4'-dimethoxytrityl)-8-N-[(4-dihydroxy-boryl (benzopinacol cyclic ester) benzoyl] amino-1,3-octanediol 3-O-(2-cyanoethyl)-N,N-diiso-propylamino phosphoramidite, a compound of the present invention.

With reference to FIGS. 6 and 7, 4-Carboxyphenylboronic acid (10.0 g, 60.2 mmoles) was dissolved in hot, anhydrous 1,4-dioxane (150 mL), treated with a small quantity of activated charcoal, and filtered through a 0.5 um glass fiber filter while still hot. The filtrate was heated to reflux, and benzopinacol (22.1 g, 60.3 mmoles) was added. The solution was refluxed one hour, then cooled to room temperature. The solvent was then removed on a rotary evaporator to give a white solid, which was crystallized from ethyl ether/hexanes at −20° C. overnight. The solid was filtered and dried in vacuo to afford 23.3 g (78% yield) of product. The purity of the product was confirmed by $^1$H NMR as well as by HPLC.

1H NMR (300 MHz, DMSO-$d_6$): δ 13.23 (broad singlet, 1H, CO$_2$H), 8.19 (doublet, 2H, ArH[benzoic acid]), 8.13 (doublet, 2H, ArH), 7.10 (multiplet, 20H, ArH [benzopinacol]). $^{13}$C NMR (75 MHz, DMSO-$d_6$): δ 167.4, 141.9, 135.4, 129.2, 128.2, 127.6, 127.4, 126.2, 96.3.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=14.9±0.1 minutes.

B. Synthesis of 4-dihydroxyboryl(benzopinacol cyclic ester) benzoic Acid NHS Ester 4-Dihydroxyboryl(benzopinacol cyclic ester)benzoic acid (17.4 g, 35.0 mmoles) was dissolved in anhydrous tetrahydrofuran (100 mL). N-hydroxysuccinimide (4.0 g, 34.8 mmoles) was added, followed by 1,3-dicyclohexylcarbodiimide (7.2 g, 34.6 mmoles). The reaction was stirred overnight at room temperature, during which time a white precipitate of 1,3-dicyclohexylurea forms. The solid was removed by filtration and washed with a little tetrahydrofuran. The combined filtrates were evaporated to dryness on a rotary evaporator to give an off-white solid. The solid was dissolved in tetrahydrofuran (100 mL), the solution was filtered, and hexanes (300 mL) were added. Crystallization was allowed to occur overnight at −20° C. The solid was filtered and dried in vacuo to afford 18.4 g (89% yield) of product. The purity of the product was confirmed by $^1$H and $^{13}$C NMR.

$^1$H NMR (300 MHz, DMSO-$d_6$): δ 8.31 (doublet, 2H, ArH[benzoic acid]), 8.25 (doublet, 2H, ArH[benzoic acid]), 7.15 (multiplet, 20H, ArH[benzopinacol]), 2.91 (singlet, 4H, CH$_2$). $^{13}$C NMR (75 MHz, DMSO-$d_6$): δ 170.4, 161.9, 141.7, 136.0, 129.7, 128.2, 127.6, 127.4, 126.2, 96.5, 25.5.

C. Synthesis of N-benzyloxycarbonyl-β-alanylserine Methyl Ester

N-Benzyloxycarbonyl-β-alanine N-hydroxysuccinimide ester (14.1 g, 44.0 mmoles; Bachem) was dissolved in 100 mL of dry N,N-dimethylformamide, and serine methyl ester hydrochloride (5.2 g, 43.6 mmoles) was added. The mixture was stirred at room temperature and N,N-diisopropylethylamine (10 mL, 57.4 mmoles) was added. The reaction was stirred overnight. The solvent was then removed on a rotary evaporator to give a clear colorless syrup. This material was partitioned between ethyl acetate (250 mL) and water (250 mL). The layers were separated, and the ethyl acetate layer was washed successively with half-saturated aqueous potassium bisulfate (200 mL, once), saturated aqueous sodium bicarbonate (200 mL, twice) and saturated aqueous sodium chloride (200 mL, once). The ethyl acetate solution was dried over anhydrous magnesium sulfate, filtered, and evaporated on a rotary evaporator to a clear colorless syrup. The syrup was dried well in vacuo to afford 10.4 g (74% yield) of an amorphous white solid. The purity of the product was confirmed by $^1$H and $^{13}$C NMR as well as by HPLC.

$^1$H NMR (300 MHz, DMSO-$d_6$): δ 8.21 (doublet, 1H, NH[serine]), 7.33 (multiplet, 5H, ArH), 7.18 (triplet, 1H, NH[β-alanine]), 5.00 (triplet, 1H, OH), 4.99 (singlet, 2H, Ar—CH$_2$O), 4.32 (multiplet, 1H, CH), 3.62 (multiplet, 2H, CH$_2$OH), 3.60 (singlet, 3H, CH$_3$), 3.18 (quartet, 2H, NHCH$_2$CH$_2$), 2.33 (triplet, 2H, NHCH$_2$CH$_2$). $^{13}$C NMR (75 MHz, DMSO-$d_6$): δ 171.0, 170.5, 155.9, 137.2, 128.2, 127.6, 127.5, 65.1, 61.1, 54.5, 51.5, 36.9, 35.2.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=9.9±0.1 minutes.

D. Synthesis of 3-O-(4,4'-dimethoxytrityl)-N-benzyloxycarbonyl-β-alanylserine Methyl Ester N-Benzyloxycarbonyl-β-alanylserine methyl ester (10.0 g, 30.8 mmoles) was dissolved in dry pyridine (100 mL) and 4,4'-dimethoxytrityl chloride (11.0 g, 32.5 mmoles) was added. The yellow solution was stirred overnight under dry nitrogen at room temperature. Methanol (10 mL) was then added and the solutions stirred and additional hour. The solvent was removed on a rotary evaporator at a bath temperature of <40° C. to give a thick yellow syrup. The syrup was partitioned between ethyl acetate (300 mL) and saturated aqueous sodium bicarbonate (150 mL). The layers were separated, and the ethyl acetate layer was washed successively with saturated aqueous sodium bicarbonate (150 mL, once) and saturated aqueous sodium chloride (150 mL, once). The ethyl acetate solution was dried over anhydrous magnesium sulfate, filtered, and concentrated to a yellow syrup on a rotary evaporator. The syrup was dissolved in ethyl acetate (100 mL) and stirred at room temperature. Hexanes (200 mL) were added slowly dropwise, and a nearly white solid precipitates. The solid was collected at −20° C. overnight, filtered, washed with a mixture (1:1, v/v) of ethyl acetate and hexanes (100 mL) and dried in vacuo to afford 17.0 g (88% yield) of product. The purity of the product was confirmed by $^1$H and $^{13}$C NMR as well as by HPLC.

$^1$H NMR (300 MHz, DMSO-$d_6$): δ 8.51 (doublet, 1H, NH[serine]), 7.39–7.21 (multiplet, 15H, ArH[DMT, Cbz] and NH[β-alanine]), 6.90 (doublet, 4H, ArH[DMT]), 5.02 (singlet, 2H, Ar—CH$_2$O), 4.60 (multiplet, 1H, CH), 3.73 (singlet, 6H, Ar—OCH$_3$), 3.64 (singlet, 3H, CO$_2$CH$_3$), 3.23 (multiplet, 4H, NHCH$_2$CH$_2$ and CHCH$_2$O), 2.43 (triplet, 2H, NHCH$_2$CH$_2$). $^{13}$C NMR (75 MHz, DMSO-$d_6$): δ 171.0, 170.7, 158.4, 156.2, 144.8, 137.3, 135.5, 135.4, 129.9, 128.5, 127.9, 127.8, 126.9, 113.2, 85.5, 65.3, 63.0, 55.0, 52.3, 51.9, 37.0, 35.2.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=15.9±0.1 minutes.

E. Synthesis of 1-O-(4,4'-dimethoxytrityl)-N-benzyloxycarbonyl-β-alanylserinol

3-O-(4,4'-Dimethoxytrityl)-N-benzyloxycarbonyl-β-alanylserine methyl ester (10.0 g, 16.0 mmoles) was dissolved in anhydrous tetrahydrofuran (100 mL). This solution was added dropwise under dry nitrogen to a stirred solution of lithium borohydride (1.0 g, 45.9 mmoles) in anhydrous tetrahydrofuran (100 mL). The clear colorless solution was stirred six hours at room temperature under dry nitrogen. Water (50 mL) was then added, and the mixture was stirred for an additional four hours. Tetrahydrofuran (200 mL) was added and a white solid precipitates. The mixture was filtered, the solid washed with a little tetrahydrofuran, and the filtrate concentrated to about 50 mL on a rotary evaporator. Ethyl acetate (250 mL) was added, and the layers were separated. The ethyl acetate solution was washed successively with saturated aqueous sodium bicarbonate (100 mL, once) and saturated aqueous sodium chloride (100 mL, once), dried over anhydrous magnesium sulfate, and filtered. The filtrate was evaporated on a rotary evaporator to a clear colorless syrup, which was further dried in vacuo over potassium hydroxide pellets to afford 9.3 g (97% yield) of a crisp, glassy foam. The purity of the product was confirmed by $^1$H and $^{13}$C NMR as well as by HPLC.

$^1$H NMR (300 MHz, DMSO-$d_6$): δ 7.80 (doublet, 1H, NH[serine]), 7.40–7.19 (multiplet, 15H, ArH[DMT, Cbz] and NH[β-alanine]), 6.88 (doublet, 4H, ArH[DMT]), 5.00 (singlet, 2H, Ar—CH$_2$O), 4.63 (triplet, 1H, CH$_2$OH), 4.01 (multiplet, 1H, CH), 3.72 (singlet, 6H, Ar—OCH$_3$), 3.45 (triplet, 2H, CHCH$_2$OH), 3.20 (quartet, 2H, NHCH$_2$CH$_2$), 2.98 (doublet of multiplets, 2H, CHCH$_2$O-DMT), 2.32 (triplet, 2H, NHCH$_2$CH$_2$). $^{13}$C NMR (75 MHz, DMSO-$d_6$): δ 170.2, 158.2, 156.2, 145.3, 137.3, 136.0, 129.9, 129.1, 128.5, 127.9, 127.6, 126.7, 113.2, 85.2, 65.2, 62.6, 60.8, 55.0, 50.9, 37.2, 35.8.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=14.8±0.1 minutes.

F. Synthesis of 1-O-(4,4'-dimethoxytrityl)-β-alanylserinol

1-O-(4,4'-Dimethoxytrityl)-N-benzyloxycarbonyl-β-alanylserinol (9.3 g, 15.5 mmoles) was dissolved in absolute methanol (200 mL). The solution was placed in a one liter Parr hydrogenation vessel, and the solution was purged with nitrogen for five minutes. Palladium on carbon catalyst (1.0 g, 10% Pd/C) slurried in ethyl acetate (20 mL) was added, and the vessel was affixed to a Parr shaker. The vessel was again purged with nitrogen, evacuated, and hydrogen was introduced to a pressure of 35 psi. The vessel was shaken for six hours at room temperature, then evacuated, filled with nitrogen and removed from the shaker. The contents were filtered through a 0.5 μm glass fiber filter, and the filtrate was evaporated to dryness on a rotary evaporator to yield a clear, colorless syrup. The syrup was further dried in vacuo over potassium hydroxide pellets to afford 7.1 g (93% yield) of a crisp, glassy foam. The purity of the product was confirmed by $^1$H and $^{13}$C NMR as well as by HPLC.

$^1$H NMR (300 MHz, DMSO-$d_6$): δ 7.87 (doublet, 1H, NH[serine]), 7.38–7.20 (multiplet, 9H, ArH), 6.88 (doublet, 4H, ArH), 3.97 (multiplet, 1H, CH), 3.72 (singlet, 6H, Ar—OCH$_3$), 3.45 (doublet, 2H, CHCH$_2$OH), 3.26 (broad singlet, 3H, NH$_2$ and OH), 2.95 (doublet of multiplets, 2H, CHCH$_2$O-DMT), 2.73 (doublet of triplets, 2H, NH$_2$CH$_2$CH$_2$), 2.19 (triplet, 2H, NH$_2$CH$_2$CH$_2$). $^{13}$C NMR (75 MHz, DMSO-$d_6$): δ 171.3, 158.3, 145.4, 136.1, 130.0, 128.0, 127.9, 126.7, 113.3, 85.3, 62.7, 60.9, 55.0, 51.0, 37.8, 37.7.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=11.0±0.1 minutes.

G. Synthesis of 1-O-(4,4'-dimethoxytrityl)-2-N-[(4-dihydroxyboryl(benzopinacol cyclic ester)-benzoyl)-β-alanyl)]serinol 1-O-(4,4'-Dimethoxytrityl)-β-alanylserinol (7.1 g, 14.4 mmoles) was dissolved in anhydrous tetrahydrofuran (100 mL) under dry nitrogen. Triethylamine (2.0 mL, 14.4 mmoles) was added, followed by 4-dihydroxyboryl (benzopinacol cyclic ester)benzoic acid N-hydroxysuccinimide ester (8.5 g, 14.4 mmoles). The reaction mixture was stirred at room temperature for twenty-four hours, filtered, and the filtrate concentrated to a thick syrup on a rotary evaporator. The syrup was dissolved in ethyl acetate (250 mL) and the solution was washed successively with saturated aqueous sodium bicarbonate (200 mL, twice) then saturated aqueous sodium chloride (200 mL, once). The solution was dried over anhydrous magnesium sulfate, filtered and evaporated to a yellow syrup on a rotary evaporator. The syrup was dissolved in ethyl acetate (60 mL) containing triethylamine (1 mL), and 10 mL aliquots of this solution are purified by preparative HPLC (Waters PrepLC 2000 system) on a column of Porasil silica (47×300 mm; Waters). The flow rate was 50 mL/minute. The following step gradient was used: 66:33:1 (v/v/v) ethyl acetate:hexanes:triethylamine for 10 minutes to elute some minor contaminants, then 98:1:1 (v/v/v) ethyl acetate:methanol:triethylamine for 20 minutes to elute the desired product. The eluent was monitored by absorbance at 270 nm. Product fractions were pooled and evaporated to dryness on a rotary evaporator to yield a clear, colorless syrup. The syrup was further dried in vacuo over potassium hydroxide pellets to afford 7.1 g (93% yield) of a crisp, glassy foam. The purity of the product was confirmed by $^1$H and $^{13}$C NMR as well as by both gradient and isocratic HPLC.

$^1$H NMR (300 MHz, DMSO-$d_6$): δ 8.64 (triplet, 1H, NH[β-alanine]), 8.09 (doublet, 2H, ArH[PBA]), 7.95 (doublet, 2H, ArH[PBA]), 7.83 (doublet, 1H, NH[serine]), 7.38–7.09 (multiplet, 30H ArH[DMT, benzopinacol]), 6.85

(doublet, 4H, ArH[DMT]), 4.68 (triplet, 1H, CHCH$_2$OH), 4.05 (multiplet, 1H, CH), 3.70 (singlet, 6H, Ar—OCH$_3$), 3.49 (multiplet, 4H, CHCH$_2$OH and NHCH$_2$CH$_2$), 2.98 (doublet of multiplets, 2H, CHCH$_2$O-DMT), 2.46 (triplet, 2H, NHCH$_2$CH$_2$). $^{13}$C NMR (75 MHz, DMSO-d$_6$): δ 166.3, 158.2, 145.3, 142.0, 141.9, 138.1, 136.0, 135.2, 129.9, 128.2, 127.9, 127.6, 127.4, 127.1, 126.7, 113.2, 96.3, 85.2, 62.6, 60.9, 55.1, 50.9, 36.3, 35.4.

HPLC (reverse phase, 4.6×100 mm C4 column, flow rate 1.0 mL/minute, linear gradient of acetonitrile in 0.1 M triethylammonium acetate, pH 6.5, 0 to 100% acetonitrile in 15 minutes, detector monitoring absorbance at 260 nm): Retention time=18.6±0.1 minutes.

HPLC (reverse phase, 4.6×100 mm C4 column, flow rate 1.0 mL/minute, isocratic elution using 7% 0.1 M triethylammonium acetate, pH 6.5:93% acetonitrile): Retention time=2.4±0.1 minutes.

H. Synthesis of 1-O-(4,4'-dimethoxytrityl)-2-N-[(4-dihydroxyboryl-(benzopinacol cyclic ester)-benzoyl)-β-alanyl)]serinol 3-O-(2-cyanoethyl)-N,N-diisopropylamino phosphoramidite 1-O-(4,4'-Dimethoxytrityl)-2-N-[(4-dihydroxyboryl (benzopinacol cyclic ester)benzoyl)-β-alanyl)]serinol (7.2 g, 7.6 mmoles) was dissolved in anhydrous dichloromethane (250 mL, filtered through basic alumina). N,N-diisopropylethylamine (5.5 mL, 31.6 mmoles) was added, and the solution was stirred under dry nitrogen at room temperature. 2-Cyanoethyl-N,N-diisopropyl-amino chlorophosphine (2.5 mL, 10.5 mmoles) was added dropwise, and the solution was stirred for one hour. The reaction mixture was then concentrated to about 50 mL on a rotary evaporator, and ethyl acetate (300 mL, pre-washed with 100 mL of saturated aqueous sodium bicarbonate) was added. The organic solution was washed with saturated aqueous sodium bicarbonate (100 mL, once) then saturated aqueous sodium chloride (100 mL, once), dried over anhydrous magnesium sulfate, and filtered. The filtrate was evaporated to dryness on a rotary evaporator to give a pale yellow glassy foam. This material was dissolved in ethyl acetate (25 mL) and hexanes (15 mL) containing triethylamine (1 mL). Five mL aliquots of this solution were purified by preparative HPLC (Waters PrepLC 2000 system) on a column of Porasil silica (40×100 mm; Waters). The flow rate was 50 mL/minute. The following multiphasic linear gradient was used: 50:49:1 (v/v/v) to 79:20:1 (v/v/v) ethyl acetate:hexanes:triethylamine over 10 minutes, to 99:1 (v/v) ethyl acetate:triethylamine over 5 minutes, to 79:20:1 ethyl acetate:methanol:triethylamine over 2 minutes, and hold at this composition for 3 minutes. The eluent was monitored by absorbance at 260 nm; the product eluted in the first major peak. Product fractions were pooled and evaporated to dryness on a rotary evaporator to yield a clear, colorless syrup. The syrup was dissolved in ethyl acetate (30 mL) plus triethylamine (2 mL), and this solution was added dropwise to rapidly stirred, ice-cold hexanes (300 mL) to produce a white precipitate. The precipitate was collected at −20° C. overnight, filtered, washed well with cold hexanes, and dried in vacuo over anhydrous potassium carbonate or afford 7.9 g (91% yield) of product. The purity of the product was confirmed by $^1$H, $^{13}$C and $^{31}$P NMR as well as by HPLC.

$^1$H NMR (300 MHz, DMSO-d$_6$): δ 8.64 (doublet of triplets, 1H, NH[β-alanine]), 8.11 (doublet, 2H, ArH[PBA]), 7.97 (doublet, 2H, ArH[PBA]), 7.95 (doublet, 1H, NH[serine]), 7.38–7.09 (multiplet, 30H, ArH[DMT, benzopinacol]), 6.85 (doublet, 4H, ArH[DMT]), 4.22 (multiplet, 1H, CH), 3.70 (singlet, 6H, Ar—OCH$_3$), 3.70–3.40 (multiplet, 8H, OCH$_2$CH$_2$CN, NCH(CH$_3$)$_2$, CHCH$_2$OP and NHCH$_2$CH$_2$), 3.02 (multiplet, 2H, CHCH$_2$O-DMT), 2.68 (doublet of triplets, 2H, OCH$_2$CH$_2$CN), 2.48 (multiplet, 2H, NHCH$_2$CH$_2$), 1.02 (doublet of doublets, 12H, NCH(CH$_3$)$_2$). $^{13}$C NMR (75 MHz, DMSO-d$_6$): δ 170.5, 166.2, 158.3, 145.2, 142.1, 142.0, 138.1, 135.9, 135.2, 129.9, 128.2, 127.9, 127.6, 127.4, 127.1, 126.8, 119.0, 113.3, 96.3, 85.4, 62.3 (broad), 58.5, 58.4, 58.3, 58.2, 42.6, 42.4, 36.3, 35.4, 31.0, 24.4, 24.3, 22.1, 19.9, 19.8. $^{31}$P NMR (121 MHz, DMSO-d$_6$): δ 147.4, 147.1 (diastereomers).

HPLC (reverse phase, 4.6×100 mm C4 column, flow rate 1.0 mL/minute, isocratic elution using 7% 0.1 M triethylammonium acetate, pH 6.5:93% acetonitrile): Retention time=4.4±0.1 minutes.

Example 4

This example illustrates the automated solid phase synthesis of boronic acid-modified oligodeoxyribonucleotides.

Oligodeoxyribonucleotide PX001 (sequence 5'-CGC CAG GGT TTT CCC AGT CAC GAC-3') was synthesized on a 1 μmole scale using standard automated phosphoramidite chemistry (Model 394 automated DNA synthesizer from Perkin Elmer/Applied Biosystems [Foster City, Calif.] and associated UltraFast DNA synthesis reagents from Glen Research [Sterling, Va.]) in the Trityl ON mode. The completed oligodeoxyribonucleotide was retained on the support. An appropriate quantity of the desired phenylboronic acid (PBA)-containing phosphoramidite was dissolved either in anhydrous acetonitrile (1-O-(4,4'-dimethoxytrityl)-8-N-[4-dihydroxyboryl-(benzopinacol cyclic ester) benzoyl)]amino-1,3-octanediol 3-O-(2-cyanoethyl)-N,N-diisopropyl-amino phosphoramidite and 1-O-(4,4'-dimethoxytrityl)-3-N-[(4-dihydroxyboryl(benzopinacol cyclic ester)benzoyl)-β-alanyl)]amino-1,2-propanediol 3-O-(2-cyanoethyl)-N,N-diisopropyl-amino phosphoramidite) or in 75:25 (v/v) anhydrous acetonitrile:anhydrous tetrahydrofuran (1-O-(4,4'-dimethoxytrityl)-2-N-[(4-dihydroxyboryl-(benzopinacol cyclic ester)benzoyl)-β-alanyl)]serinol 3-O-(2-cyanoethyl)-N,N-diisopropylamino phosphoramidite) to give a final concentration of 0.1 M. This solution was placed on the DNA synthesizer in one of the extra phosphoramidite bottle positions. One or more PBA moieties were then added onto the 5'-end of the oligodeoxyribonucleotide using a modification of the standard coupling cycle in which the "wait time" for the coupling reaction had been extended to fifteen minutes. Again, the synthesis was carried out in the Trityl ON mode. Coupling yields for the addition of the PBA amidites to the oligodeoxyribonucleotide were estimated to be >95% from the collected trityl solutions of each cycle and from subsequent analytical HPLC.

The completed tritylated, PBA-modified oligodeoxyribonucleotide was then cleaved from the support with concentrated ammonium hydroxide on the instrument according to the manufacturer's protocol. The protecting groups on the nucleobases and the boronic acid(s) were simultaneously removed by heating the ammonium hydroxide solution in a heating block at 60° C. for one hour. This solution was then cooled to 4° C. in a refrigerator and concentrated to about 1 mL in a SpeedVac vacuum concentrator (Savant Instruments [Farmingdale, N.Y.]). The solution containing the crude PBA-modified oligodeoxyribonucleotide was stored at 4° C. until it could be purified by high performance liquid chromatography.

Example 5

This example illustrates the purification of boronic acid-modified oligodeoxyribonucleotides.

Crude tritylated, boronic acid-modified oligodeoxyribonucleotides were purified by reverse phase HPLC using modifications of methods commonly used to purify synthetic oligodeoxyribonucleotides. However, the C18 and C8 phases commonly used to purify tritylated unmodified oligodeoxyribonucleotides and labeled oligodeoxyribonucleotides performed poorly with the tritylated, boronic acid-modified oligodeoxyribonucleotides. Peaks associated with the desired products were very broad, tailed badly, and as such were poorly resolved from impurities. It was found that C4 phases performed better and gave satisfactory results.

An aliquot (10–100 μL) of the above solution of crude tritylated, boronic acid-modified oligodeoxyribonucleotides was injected onto a 4.6 mm×150 mm C4 column (Inertsil 5 μm, MetaChem Technologies [Torrance, Calif.]) coupled to a Hewlett Packard Series 1050 liquid chromatograph. A biphasic linear gradient of acetonitrile (component B) in 0.1 M triethyl-ammonium acetate, pH 6.5 (Component A), was used to develop the chromatogram. The gradient was as follows: 95:5 (v/v) A:B to 65:35 (v/v) A:B over 21 minutes, then to 10:90 (v/v) A:B over 3 minutes. The flow rate was 1.0 ml/minute, and UV detection at 280 nm was used to observe the separation. The product oligodeoxyribonucleotides eluted from the column at 18–22 minutes, with longer retention times corresponding to increased numbers of PBA moieties. The product was collected and evaporated to dryness in the SpeedVac to give an oily pellet. The pellet was dissolved in 1 mL of 80:20 (v/v) glacial acetic acid:water and allowed to sit at room temperature for one hour to remove the trityl group. The solution was again evaporated to dryness in the SpeedVac to give an oily pellet. The pellet was dissolved in 0.5 mL of water and stored frozen. A 10 μL aliquot was analyzed by HPLC using the above column and gradient. Purities of boronic acid-modified oligodeoxyribonucleotides obtained by this procedure were generally >90% (see FIG. 8 below).

All publications, patents and patent applications mentioned in this specification were herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of the formula

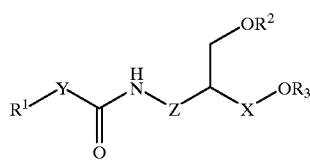

wherein:

$R^1$ is an aryl boronic acid ester moiety;

Y is a member selected from the group consisting of $O(CH_2)_m$, $S(CH_2)_m$, and a carbon-carbon single bond, wherein m is an integer of 1 to 5;

Z is a member selected from the group consisting of alkylene, alkyleneamido, alkyleneamidoalkylene and alkyleneamidoalkyleneamido having between 1 and 16 carbons atoms;

X is a member selected from the group consisting of a methylene group and a carbon-carbon single bond;

$R^2$ is a member selected from the group consisting of hydrogen, trityl, monomethoxytrityl and dimethoxytrityl; and $R^3$ is a member selected from the group consisting of hydrogen and an activated phosphorous moiety.

2. A compound in accordance with claim 1, wherein $R^1$ is a phenyl boronic acid ester moiety.

3. A compound in accordance with claim 2, wherein said phenyl boronic acid ester moiety is a member selected from the group consisting of

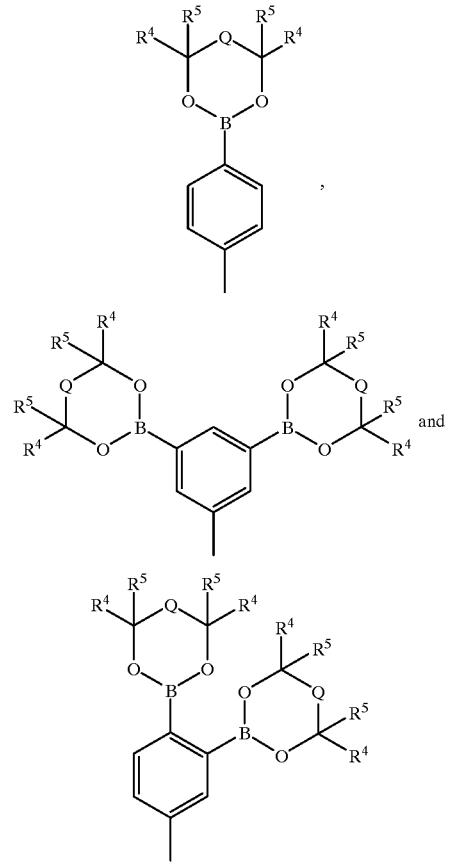

wherein:

$R^4$ and $R^5$ are members independently selected from the group consisting of hydrogen, methyl and phenyl; and Q is a member selected from the group consisting of a methylene group and a carbon-carbon single bond.

4. A compound in accordance with claim 1, wherein Y is a carbon—carbon single bond.

5. A compound in accordance with claim 1, wherein Y is $O(CH_2)_m$ and m is 1.

6. A compound in accordance with claim 1, wherein Y is $S(CH_2)_m$ and m is 1.

7. A compound in accordance with claim 1, wherein Z is $C_1$–$C_5$ alkylene.

8. A compound in accordance with claim 1, wherein Z is $C_1$–$C_2$ alkyleneamido.

9. A compound in accordance with claim 1, wherein X is a methylene group.

10. A compound in accordance with claim 1, wherein X is a carbon—carbon single bond.

11. A compound in accordance with claim 3, wherein

R$^2$ is dimethoxytrityl; and

R$^3$ is a phosphoramidite.

12. A compound in accordance with claim 3, wherein Q is a methylene group.

13. A compound in accordance with claim 11, wherein said phosphoramidite is β-cyanoethyl-N-diisopropylamino phosphoramidite.

14. A compound in accordance with claim 13, wherein said compound is 1-O-(4,4'-dimethoxytrityl)-2-N-[(4-dihydroxyboryl(benzopinacol cyclic ester)benzoyl)-β-alanyl)]serinol 3-O-(2-cyanoethyl)-N,N-diisopropylamino phosphoramidite.

* * * * *